US011110641B2

(12) United States Patent
Hayakawa et al.

(10) Patent No.: US 11,110,641 B2
(45) Date of Patent: Sep. 7, 2021

(54) METHOD AND APPARATUS FOR STERILIZING PREFORM

(71) Applicant: Dai Nippon Printing Co., Ltd., Tokyo (JP)

(72) Inventors: Atsushi Hayakawa, Tokyo (JP); Yuiko Wada, Tokyo (JP)

(73) Assignee: Dai Nippon Printing Co., Ltd., Tokyo (JP)

( * ) Notice: Subject to any disclaimer, the term of this patent is extended or adjusted under 35 U.S.C. 154(b) by 149 days.

(21) Appl. No.: 16/310,117

(22) PCT Filed: Jun. 21, 2017

(86) PCT No.: PCT/JP2017/022911
§ 371 (c)(1),
(2) Date: Dec. 14, 2018

(87) PCT Pub. No.: WO2017/221991
PCT Pub. Date: Dec. 28, 2017

(65) Prior Publication Data
US 2019/0176385 A1 Jun. 13, 2019

(30) Foreign Application Priority Data

Jun. 24, 2016 (JP) .............................. JP2016-125568
Aug. 5, 2016 (JP) .............................. JP2016-154745
Oct. 20, 2016 (JP) .............................. JP2016-206130

(51) Int. Cl.
*A61L 2/00* (2006.01)
*B08B 7/00* (2006.01)
(Continued)

(52) U.S. Cl.
CPC ................ *B29C 49/46* (2013.01); *A61L 2/10* (2013.01); *A61L 2/208* (2013.01); *B29C 49/42* (2013.01);
(Continued)

(58) Field of Classification Search
CPC ........ A61L 2/00; A61L 2/0047; A61L 2/0082; A61L 2/0094; A61L 2/20; A61L 2/208; A61L 2/24; A61L 2202/11; B65B 55/00
(Continued)

(56) References Cited

U.S. PATENT DOCUMENTS 5,011,664 A * 4/1991 Olanders ............... B65B 55/103
422/292
6,562,281 B1 5/2003 Marchau et al.
(Continued)

FOREIGN PATENT DOCUMENTS

DE  10 2013 101 407 A1   8/2014
EP     2 394 950 A1   12/2011
(Continued)

OTHER PUBLICATIONS

European Patent English Translation of The Description and The Claims Sections of JP 2010-507503 A.*
(Continued)

*Primary Examiner* — Monzer R Chorbaji
(74) *Attorney, Agent, or Firm* — Burr & Brown, PLLC

(57) ABSTRACT

To provide a method and an apparatus for sterilizing a preform that can reduce the amount of the remaining hydrogen peroxide in sterilization of a preform, a sterilizer at least containing 30% by mass or less of hydrogen peroxide and a solvent having a boiling point of 85° C. or lower is gasified, the sterilizer gas is blasted to the preform, and the preform to which the sterilizer has been blasted is heated to a temperature suitable for molding by blasting hot air or without blasting hot air. Alternatively, after the preform is irradiated with light containing ultraviolet rays, the sterilizer gas is blasted to the preform, and the preform is heated to a temperature suitable for molding.

20 Claims, 12 Drawing Sheets

(51) Int. Cl.
*B08B 9/00* (2006.01)
*B29C 49/46* (2006.01)
*B29C 49/42* (2006.01)
*B29C 49/64* (2006.01)
*A61L 2/10* (2006.01)
*A61L 2/20* (2006.01)

(52) U.S. Cl.
CPC .......... *B29C 49/64* (2013.01); *B29C 49/6418* (2013.01); *B29C 2049/4682* (2013.01)

(58) Field of Classification Search
USPC ......... 422/1, 24, 28, 32, 292, 295–300, 302, 422/305, 307–308; 134/6, 22.1, 23, 26, 134/44, 61
See application file for complete search history.

(56) References Cited

U.S. PATENT DOCUMENTS

| | | |
|---|---|---|
| 2008/0152538 A1 | 6/2008 | Quetel et al. |
| 2009/0317506 A1 | 12/2009 | Adriansens |
| 2010/0047120 A1 | 2/2010 | Adriansens et al. |
| 2011/0133370 A1 | 6/2011 | Engelhard et al. |
| 2013/0078327 A1 | 3/2013 | Adriansens |
| 2014/0144105 A1 | 5/2014 | Hayakawa et al. |
| 2016/0002018 A1 | 1/2016 | Clusserath |
| 2016/0200028 A1 | 7/2016 | Lewin et al. |
| 2016/0257055 A1 | 9/2016 | Hayakawa et al. |
| 2016/0263269 A1 | 9/2016 | Hayakawa et al. |
| 2016/0325482 A1 | 11/2016 | Hayakawa et al. |

FOREIGN PATENT DOCUMENTS

| | | | |
|---|---|---|---|
| JP | H07-315345 A1 | 12/1995 | |
| JP | 2000-326935 A1 | 11/2000 | |
| JP | 2001-171623 A1 | 6/2001 | |
| JP | 2001-510104 A1 | 7/2001 | |
| JP | 2001-225814 A1 | 8/2001 | |
| JP | 2003-072719 A1 | 3/2003 | |
| JP | 2008-183899 A1 | 8/2008 | |
| JP | 2008-546605 A1 | 12/2008 | |
| JP | 2010-507503 A * | 3/2010 | ............... A61L 2/04 |
| JP | 2010-507503 A1 | 3/2010 | |
| JP | 2012-500135 A1 | 1/2012 | |
| JP | 2013-035561 A1 | 2/2013 | |
| JP | 2013-035562 A1 | 2/2013 | |
| JP | 2014-084139 A1 | 5/2014 | |
| JP | 2015-116814 A1 | 6/2015 | |
| JP | 2015-116816 A1 | 6/2015 | |
| JP | 2015-171812 A1 | 10/2015 | |
| JP | 2016-055915 A1 | 4/2016 | |
| JP | 2016-137629 A1 | 8/2016 | |
| JP | 2016-141400 A1 | 8/2016 | |
| JP | 2016-528078 A1 | 9/2016 | |
| WO | 2010/012915 A1 | 2/2010 | |
| WO | 2013/099789 A1 | 7/2013 | |

OTHER PUBLICATIONS

International Search Report and Written Opinion (Application No. PCT/JP2017/022911) dated Jul. 18, 2017.
Extended European Search Report, European Application No. 17815459.7, dated Jan. 28, 2020 (7 pages).
Catalogue des Fiches—SBO Universal—SBO 14/20—No. 11155, Nov. 8, 2012 (Sidel).
Manuel Utilisateur—SBO Universal—SBO 14/20—No. 11155, Mar. 3, 2009 (Sidel).
Invoice dated Feb. 17, 2009 (Gebo Packaging Solutions France SAS).
European Third Party Observation (Application No. 17815459.7) dated Mar. 17, 2021.

* cited by examiner

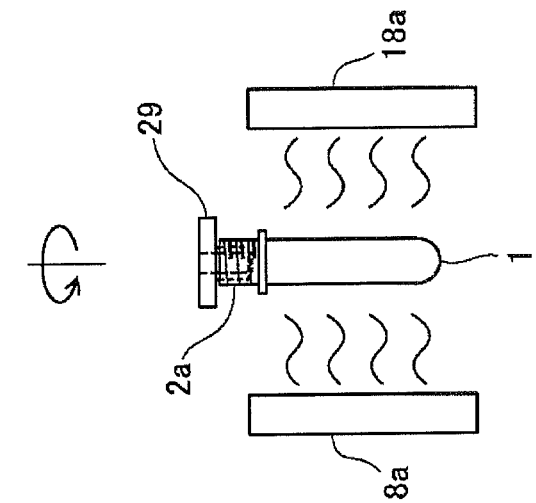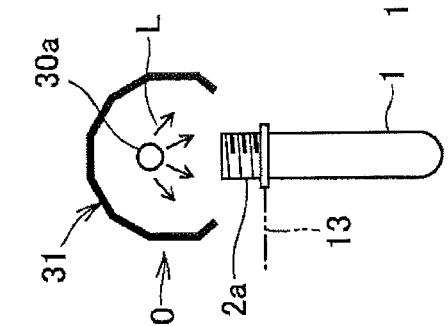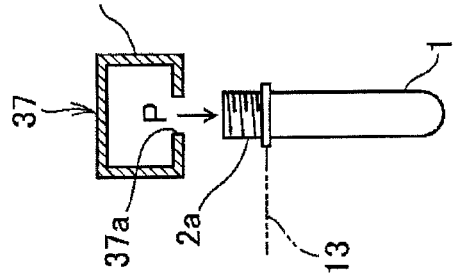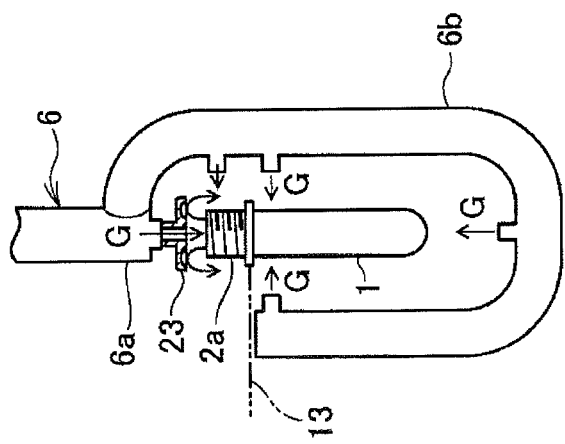

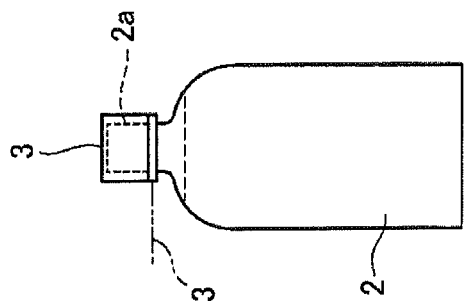
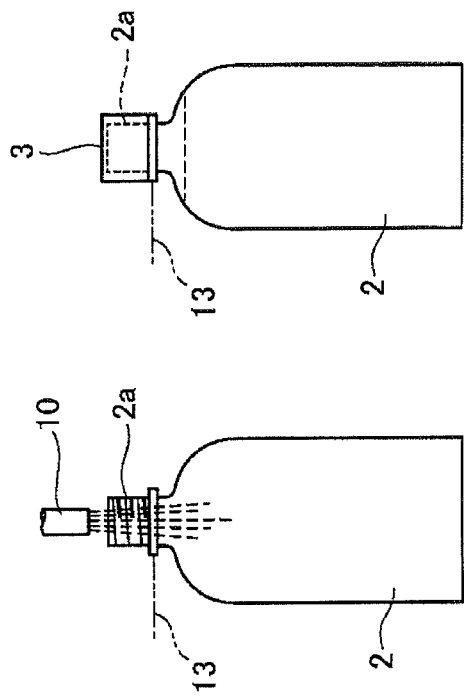
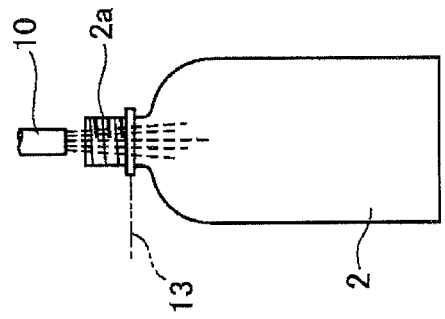
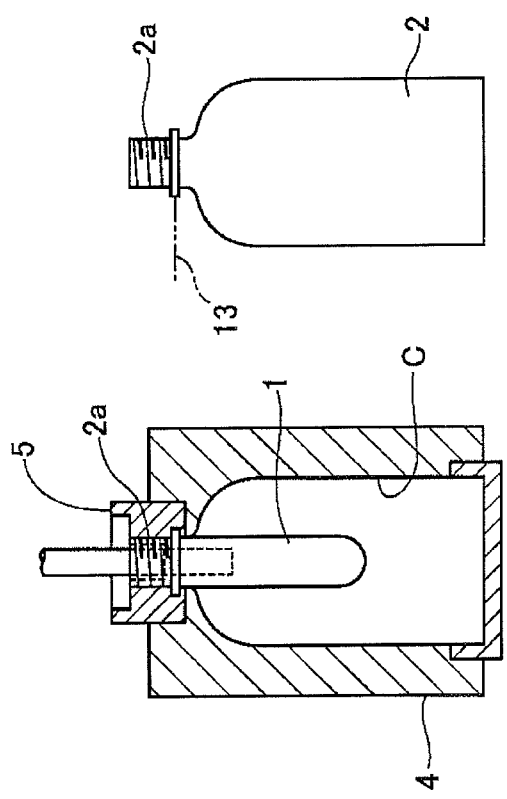

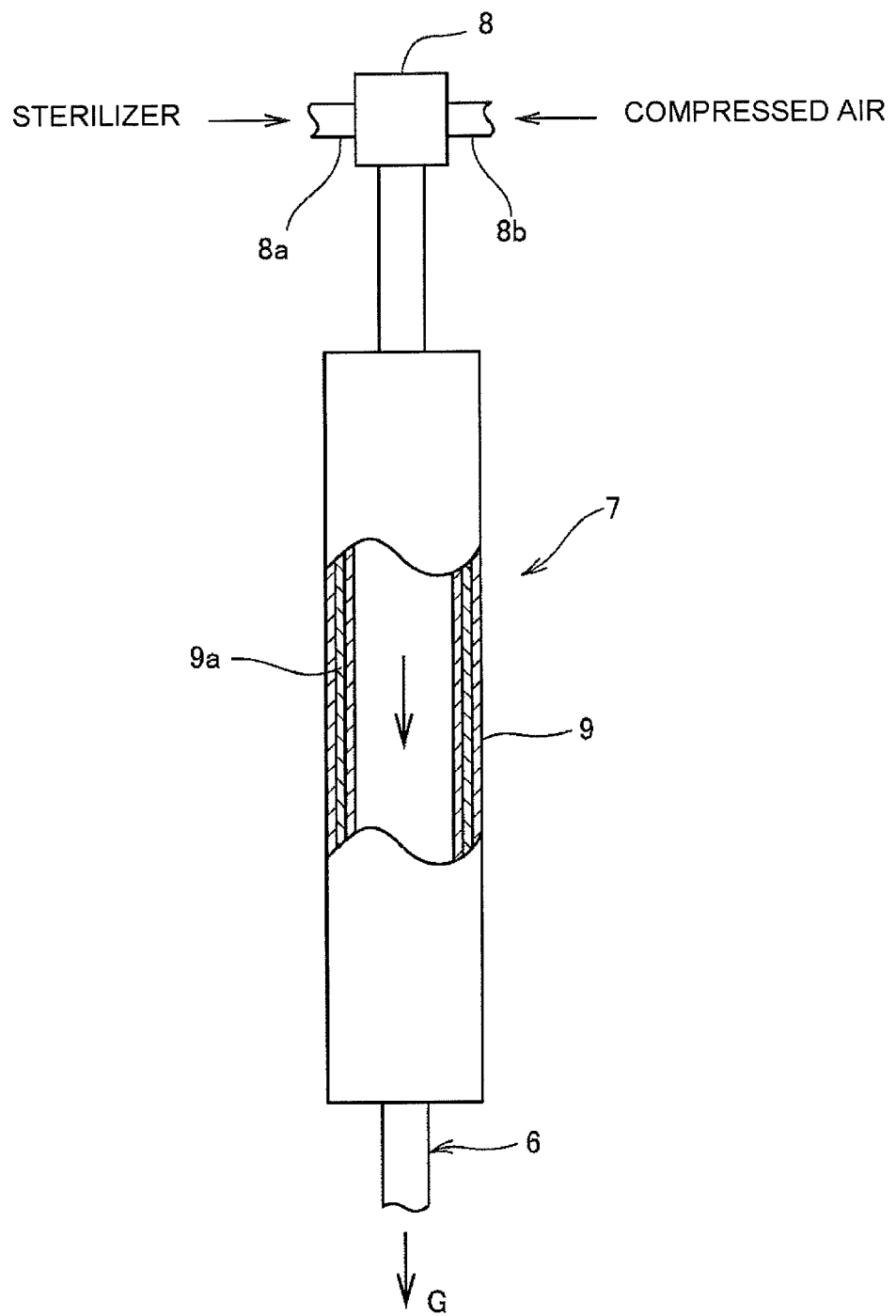

SUPPLY OF ASEPTIC AIR

METHOD AND APPARATUS FOR STERILIZING PREFORM

TECHNICAL FIELD

The present invention relates to a method and an apparatus for sterilizing a preform.

BACKGROUND ART

In conventional art, there is proposed a sterilization method in which, while a preform is continuously conveyed, a sterilizer is applied to the preform, the preform is then introduced into a heating furnace and heated in the heating furnace to a temperature suitable for molding the preform into a container, and the sterilizer applied to the preform is simultaneously dried and activated by the heating (see Patent Literatures 1, 2, and 3).

Furthermore, there is also proposed a drink filling method in which a preform is preliminarily heated, hydrogen peroxide mist or gas is blasted to the preliminarily heated preform, the preform is then heated to a temperature suitable for molding thereof, the preform of the temperature suitable for molding is molded into a bottle in a blow-molding die that is continuously traveling with the preform, the resulting bottle is removed from the blow-molding die, and the bottle is then filled with a drink and sealed with a lid (see Patent Literatures 4 and 5).

The sterilizer used in the conventional art described above is a hydrogen peroxide solution. It is also proposed to apply a sterilizer containing hydrogen peroxide and a solvent that is a liquid having a boiling point lower than 100° C. to a preform or bottle made of polyethylene terephthalate (PET) and to use a sterilizer containing 25% by mass of hydrogen peroxide and ethanol (see Patent Literatures 6 and 7).

It is also proposed to sterilize a preform by light, instead of hydrogen peroxide (see Patent Literature 8).

CITATION LIST

Patent Literature

Patent Literature 1: Japanese Unexamined Patent Publication No. 2001-510104
Patent Literature 2: Japanese Patent Laid-open Publication No. 2008-183899
Patent Literature 3: Japanese Unexamined Patent Publication No. 2008-546605
Patent Literature 4: Japanese Patent Laid-open Publication No. 2013-35561
Patent Literature 5: Japanese Patent Laid-open Publication No. 2013-35562
Patent Literature 6: International Publication No. WO2013/0099789
Patent Literature 7: Japanese Patent Laid-open Publication No. H07-315345
Patent Literature 8: Japanese Patent Laid-open Publication No. 2016-55915

SUMMARY OF INVENTION

Technical Problem

Conventional aseptic filling machines for bottles mold a preform into a bottle and sterilize the molded bottle. Such machines require much sterilizer and are too large in size. In view of this, aseptic filling machines that sterilize preforms are becoming popular. In this trend, propositions concerning sterilization of preforms, such as those disclosed in the patent literatures listed above, are made. Patent Literatures 1, 2 and 3 propose methods of spraying a hydrogen peroxide solution as a sterilizer to a preform and then directly introducing the preform into a heating furnace for heating.

The conventional techniques of sterilizing a preform described above involve sterilizing a preform yet to be molded into a bottle. Hydrogen peroxide applied to the preform for sterilization is decomposed or volatilized by the heating of the preform in the heating furnace. However, some of the hydrogen peroxide remains on the preform. The preform is then blow-molded into a bottle. Although the remaining hydrogen peroxide is further reduced in the blow-molding step, some may still remain on the inner surface of the bottle. The bottle is rinsed with aseptic water or aseptic air before the bottle is filled with a drink, and in this step, the remaining hydrogen peroxide is further reduced. However, any trace amount of hydrogen peroxide remaining in the bottle may be mixed with the drink in the bottle. To avoid this, in sterilization of a preform, the hydrogen peroxide remaining on the preform needs to be reduced as far as possible.

Furthermore, the hydrogen peroxide solution sprayed to the surface of the preform needs to form a uniform coating film. If the hydrogen peroxide solution sprayed to the surface of the preform forms a nonuniform coating film, the preform has different temperatures in different parts when heated in the heating furnace, because of the difference in heat of vaporization of the hydrogen peroxide solution. As a result, whitening, distortion, uneven molding or other molding defects may occur on the molded bottle. Furthermore, if the concentration of the hydrogen peroxide on the surface of the preform is low, or the surface of the preform is partially not coated with the hydrogen peroxide solution, sterilization may be insufficient.

Patent Literature 6 proposes to use, as a sterilizer, a hydrogen peroxide solution mixed with a solvent having a lower boiling point than water. This technique requires a step of removing the sterilizer after sprayed. That is, this technique has a drawback that it requires more steps than the methods in which the preform is directly introduced into the heating furnace.

The sterilized preform is molded into a bottle, and the bottle is filled with a drink in an aseptic atmosphere to provide a finished product. However, if the mouth portion of the preform shrinks or is deformed before the preform is molded into the bottle, bacteria may be mixed into the product from outside, and the aseptic condition of the drink may be compromised. To prevent shrinkage or deformation of the mouth portion of the preform, the mouth portion has to be kept at a temperature equal to or lower than 70° C. Since the heating of the mouth portion is thus limited, sterilization of the mouth portion of the preform requires a larger amount of hydrogen peroxide than sterilization of the body portion and the bottom portion, and therefore, an excessive amount of sterilizer containing hydrogen peroxide has to be applied or sprayed to the whole of the preform. As a result, the amount of the remaining hydrogen peroxide increases.

Although a method of sterilizing a preform without using hydrogen peroxide is also proposed, sterilization is insufficient according to the method. There is a demand for a method for sterilizing a preform that uses hydrogen peroxide to achieve high sterilization performance and reduces the amount of remaining hydrogen peroxide.

The present invention has been devised to solve the problems described above, and an object of the present invention is to provide a method and an apparatus for sterilizing a preform that can reduce the amount of remaining hydrogen peroxide in sterilization of the preform.

Solution to Problem

A method for sterilizing a preform according to the present invention is a method including a sterilizer gas blasting step of gasifying a sterilizer at least containing 30% by mass or less of hydrogen peroxide and a solvent having a boiling point of 85° C. or lower and blasting the sterilizer gas to the preform.

In the method for sterilizing a preform according to the present invention, it is preferable that the method further includes a heating step of heating the preform to which the sterilizer gas has been blasted to a temperature for molding the preform into a bottle.

In the method for sterilizing a preform according to the present invention, it is preferable that the sterilizer is a solution containing 0.5% by mass to 30% by mass of a hydrogen peroxide.

In the method for sterilizing a preform according to the present invention, it is preferable that the solvent is ethanol.

In the method for sterilizing a preform according to the present invention, it is preferable that the sterilizer is a solution containing 0.5% by mass to 30% by mass of a hydrogen peroxide constituent and 14% by mass to 99% by mass of ethanol.

In the method for sterilizing a preform according to the present invention, it is preferable that the method further includes a light irradiation step of irradiating at least a mouth portion of the preform with light containing ultraviolet rays.

A method for sterilizing a preform according to the present invention is a method including a light irradiation step of irradiating at least a mouth portion of the preform with light containing ultraviolet rays, and a sterilizer gas blasting step of gasifying a sterilizer containing at least hydrogen peroxide and blasting the sterilizer gas to the preform.

In the method for sterilizing a preform according to the present invention, it is preferable that the sterilizer gas is generated by spraying the sterilizer into an evaporating portion, and is blasted to the preform from a nozzle of the evaporating portion.

In the method for sterilizing a preform according to the present invention, it is preferable that the nozzle or a plurality of the nozzles is opposed to a traveling path of the preform, and the sterilizer gas is blasted to the preform from the nozzle or the nozzles.

In the method for sterilizing a preform according to the present invention, it is preferable that the sterilizer gas is divided into a plurality of flows in the nozzle, one of the flows is directed to the mouth portion of the preform, and another of the flows is directed to an outer surface of the preform.

In the method for sterilizing a preform according to the present invention, it is preferable that after the sterilizer gas is blasted to the preform, air is blasted to a part of the preform to which the sterilizer gas has been blasted.

In the method for sterilizing a preform according to the present invention, it is preferable that the air is hot air.

In the method for sterilizing a preform according to the present invention, it is preferable that the light containing ultraviolet rays is light emitted by a xenon flash lamp.

In the method for sterilizing a preform according to the present invention, it is preferable that the mouth portion of the preform is intensively irradiated with the light containing ultraviolet rays.

An apparatus for sterilizing a preform according to the present invention is an apparatus including a transfer device that transfers the preform from a stage of supplying the preform to a stage of molding the preform into a bottle, a nozzle that blasts a sterilizer gas to the preform on the transfer device, and a lamp that irradiates at least a mouth portion of the preform with light containing ultraviolet rays.

In the apparatus for sterilizing a preform according to the present invention, it is preferable that the nozzle is a nozzle that blasts, to the preform, the sterilizer gas at least containing 30% by mass or less of hydrogen peroxide and a solvent having a boiling point of 85° C. or lower.

In the apparatus for sterilizing a preform according to the present invention, it is preferable that the sterilizer is a solution containing 0.5% by mass to 30% by mass of a hydrogen peroxide constituent and 14% by mass to 99% by mass of ethanol.

In the apparatus for sterilizing a preform according to the present invention, it is preferable that an air nozzle that blasts air to the preform is arranged downstream of the nozzle along the transfer device.

In the apparatus for sterilizing a preform according to the present invention, it is preferable that the air nozzle has a slit-shaped blasting port that blasts the air to an opening of the preform, and the blasting port extends along a direction of transfer of the preform.

In the apparatus for sterilizing a preform according to the present invention, it is preferable that the nozzle is disposed at a tip end part of an evaporating portion that gasifies the sterilizer by spraying the sterilizer.

In the apparatus for sterilizing a preform according to the present invention, it is preferable that the nozzle that feeds the sterilizer gas is divided into a plurality of pipelines, a discharge port of one of the pipelines is opposed to an opening of the preform, another of the pipelines extends along an outer surface of the preform, and a discharge port of the another pipeline is opposed to the outer surface of the preform.

In the apparatus for sterilizing a preform according to the present invention, it is preferable that the lamp that emits the light containing ultraviolet rays is a xenon flash lamp.

In the apparatus for sterilizing a preform according to the present invention, it is preferable that the apparatus further includes a reflector plate arranged on a side of the lamp that emits the light opposite to the preform.

In the apparatus for sterilizing a preform according to the present invention, it is preferable that the reflector plate is arranged to cover the mouth portion of the preform.

Advantageous Effects of Invention

The method for sterilizing a preform according to the present invention includes a sterilizer gas blasting step of gasifying a sterilizer at least containing 30% by mass or less of hydrogen peroxide and a solvent having a boiling point of 85° C. or lower and blasting the sterilizer gas to the preform. Even though the sterilizer has a low hydrogen peroxide concentration of 30% by mass or less, by using the solvent having a boiling point of 85° C. or lower, a sufficient sterilizing power can be achieved, the amount of the hydrogen peroxide remaining on the preform can be reduced, and as a result, the amount of the hydrogen peroxide remaining on the bottle blow-molded from the preform can be reduced.

Furthermore, since the method according to the present invention includes a light irradiation step of irradiating the preform with light containing ultraviolet rays, the sterilization effect is improved, and therefore, the concentration of hydrogen peroxide, which is a sterilizing constituent, in the sterilizer can be reduced. As a result, the amount of the hydrogen peroxide remaining on the preform can be reduced.

Furthermore, according to the present invention, since the mouth portion of the preform is intensively irradiated with the light containing ultraviolet rays, the mouth portion of the preform, which is the hardest part of the preform to sterilize, can be efficiently sterilized. Therefore, the hydrogen peroxide concentration and amount of the sterilizer blasted to the whole of the preform can be further reduced, and as a result, the amount of the hydrogen peroxide remaining on the preform can be reduced.

BRIEF DESCRIPTION OF DRAWINGS

FIGS. 2(A)-2(D) illustrate a method for sterilizing a preform according to an embodiment of the present invention: FIG. 2(A) shows a sterilizer gas blasting step for the preform, FIG. 2(B) shows an air blasting step for the preform, FIG. 2(C) shows a light irradiation step for the preform, and FIG. 2(D) shows a heating step for the preform.

FIG. 3(E) shows a molding step for the preform, FIG. 3(F) shows a removal step for the bottle, FIG. 3(G) shows a content filling step for the bottle, and FIG. 3(H) shows a sealing step for the bottle.

FIG. 4 is a vertical cross-sectional view of an example of a gas generator for generating a sterilizer gas.

FIG. 6(A) is a plan view of the air nozzle, and FIG. 6(B) is a vertical cross-sectional view of the air nozzle.

DESCRIPTION OF EMBODIMENTS

In the following, a first embodiment of the present invention will be described with reference to the drawings.

First Embodiment

First, a process from sterilization of a preform to molding of the preform into a bottle and an apparatus therefor will be described with reference to FIGS. 1, 2 and 3, and a method and apparatus for sterilizing the preform will then be described in detail. According to the first embodiment, an aseptic preform can be obtained by sterilizing the preform, the amount of hydrogen peroxide remaining in the bottle molded from the preform can be reduced.

(Overview of Method and Apparatus)

Figure 1:
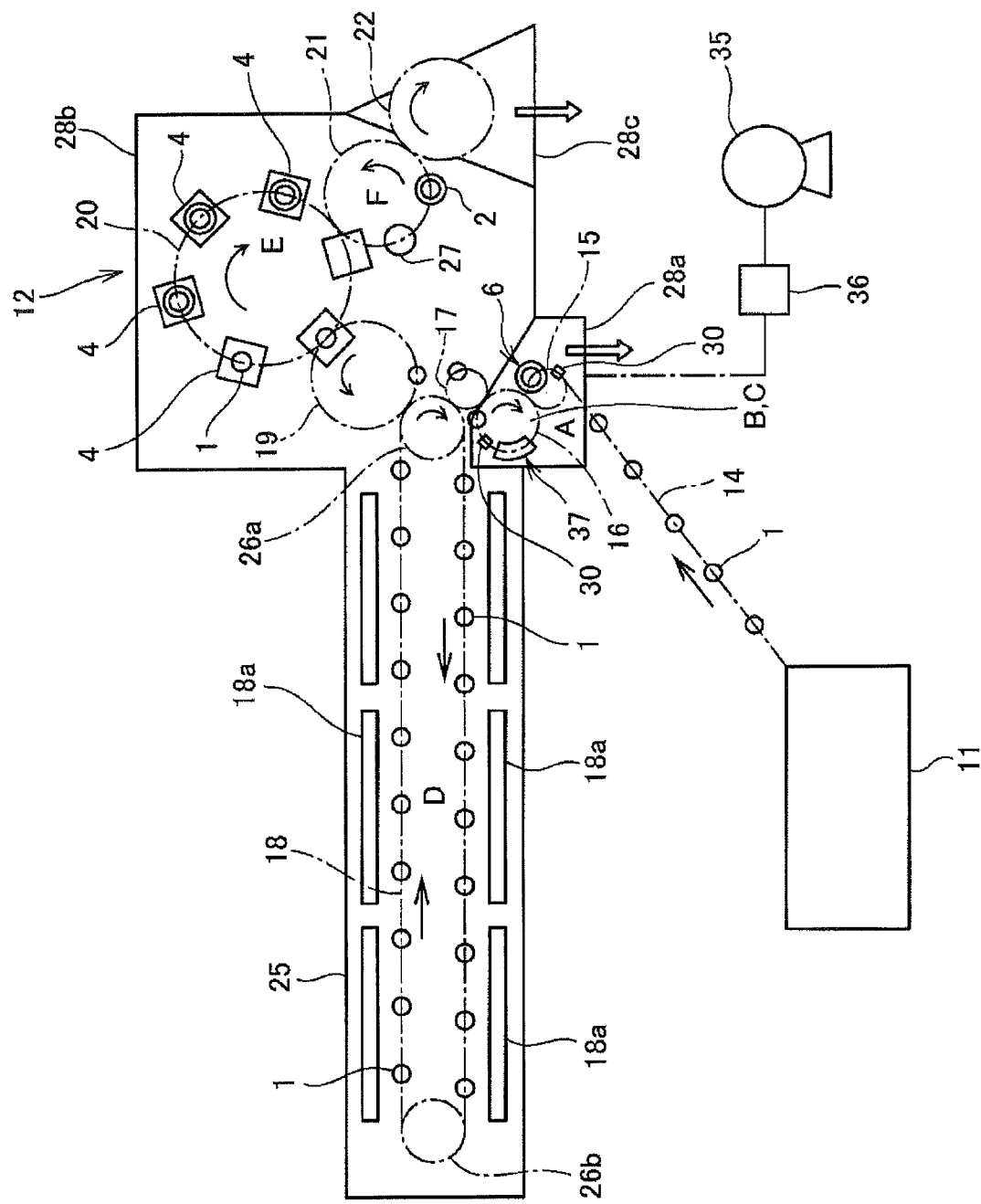
FIG. 1 is a schematic plan view of an aseptic filling system incorporating an apparatus for sterilizing a preform according to the present invention illustrating a process up to molding of the preform into a bottle.

As shown in FIG. 1, a preform 1 is fed from a preform feeding apparatus 11 and conveyed into a chamber 28*a* by a preform conveyor 14.

The preform 1 is passed to a sterilizer gas blasting wheel 15, and as shown in FIG. 2(A), a sterilizer gas blasting nozzle 6 blasts a sterilizer gas G to the preform 1 (sterilizer gas blasting step).

Then, the preform 1 is passed to an air blasting and light irradiation wheel 16, and as shown in FIG. 2(B), an air nozzle 37 blasts air P to the preform 1.

As shown in FIG. 2(C), the preform 1 is irradiated with light L containing ultraviolet rays emitted by a lamp 30*a* incorporated in a light irradiation apparatus 30 (light irradiation step).

The lamp 30*a* used for irradiating the preform 1 with light in the light irradiation step may travel in parallel with the preform 1 or may be inserted into the preform 1. The main purpose of the light irradiation is to sterilize a mouth portion 2*a*, so that the lamp 30*a* may be inserted to the same horizontal level as a gripper 13 or to a bottom of the preform 1. If the distance of insertion of the lamp 30*a* is short, the apparatus can advantageously be compact even if the process speed is raised.

Although the blasting (A) of the sterilizer gas G to the preform 1 (the sterilizer gas blasting step) is essential, the blasting (B) of air P and the irradiation (C) with the light L (the light irradiation step) are optional. However, all these steps are desirably performed. Although the blasting of the sterilizer gas G to the preform 1 and the blasting of air P are performed in this order, the light irradiation (C) can be performed at any time.

That is, along the sterilizer gas blasting wheel 15, the light irradiation apparatus 30 may be disposed upstream or downstream of the nozzle 6 or downstream of the air nozzle 37. Furthermore, a plurality of light irradiation apparatuses 30 may be arranged at a plurality of these three locations. Furthermore, the blasting (A) of the sterilizer gas G, the blasting (B) of air P, and the irradiation (C) with the light L may be performed on a single wheel or different wheels.

The sterilized preform 1 is released from the gripper 13 of a heating furnace conveying wheel 17, which has grasped the preform 1 being conveyed by the sterilizer gas blasting wheel 15, and conveyed to a heating furnace 25 by the heating furnace conveying wheel 17.

The preform 1 having entered the heating furnace 25 is heated by an infrared heater 18*a* or other heating device to a temperature suitable for a subsequent blow-molding, as shown in FIG. 2(D). The temperature is about 90° C. to 130° C.

The mouth portion 2*a* of the preform 1 is kept at a temperature equal to or less than 70° C. for preventing deformation or the like.

As shown in FIG. 2(D), the preform 1 is conveyed in the heating furnace 25 while rotating on a spindle 29 inserted in the mouth portion 2*a*. A mandrel may be inserted in the preform 1 instead of the spindle 29 to allow the preform 1 to be rotated and conveyed in an inverted position.

The heated preform 1 is released from the spindle 29, grasped by a gripper 13 on a wheel 19 in a blow-molding machine 12, and conveyed from the wheel 19 to a molding wheel 20 in the blow-molding machine. As shown in FIG. 3(E), the preform 1 is blow-molded into a bottle 2 in a mold 4 provided on the molding wheel 20. A plurality of molds 4 and a plurality of blow nozzles 5 are arranged around the molding wheel 20, and rotate around the wheel 20 at a constant speed as the wheel 20 rotates. When the heated preform 1 arrives at the mold 4, the preform 1 is received in the mold 4. The blow nozzle 5 is inserted into the preform 1, and air or other gas is blasted from the blow nozzle 5 into the preform 1 to shape the preform 1 into the bottle 2 in the mold 4. As shown in FIG. 3(F), the molded bottle 2 is grasped by a gripper 13 provided on a wheel 21 and removed from the mold 4.

Appearance inspection of the bottle 2 is performed by an inspection apparatus 27 provided on the wheel 21. The inspection apparatus 27 is a well-known apparatus and therefore will not be described in detail.

The inspected bottle 2 is conveyed to a filling section by a wheel 22.

The filling section is located in an aseptic chamber. In the filling section, the aseptic bottle 2 is filled with an aseptic content from a filling nozzle 10 in an aseptic atmosphere as shown in FIG. 3(G), and the filled bottle 2 is sealed with an aseptic cap 3 as shown in FIG. 3(H). The filling section is a well-known apparatus and therefore will not be described in detail.

(Details of Method and Apparatus)

The preform 1 according to the present invention is a bottomed tubular body similar to a test tube and is formed with a mouth portion 2a similar to the mouth portion of the bottle 2 shown in FIG. 3(H) in the early state of molding of the preform 1. A male thread is formed on the mouth portion 2a at the same time as molding of the preform 1. The preform 1 is molded by injection molding, compression molding or the like. The material of the preform 1 is a thermoplastic resin such as polyethylene terephthalate, polyethylene naphthalate, polypropylene or polyethylene or a mixture thereof and may contain a recycled thermoplastic resin. To have a barrier property, the preform 1 may contain a thermoplastic resin such as ethylene vinyl alcohol copolymer or polyamide containing aromatic amine such as metaxylylene diamine as a monomer, in the form of a layer or as an additive.

The sterilizer at least contains 30% by mass or less of hydrogen peroxide and a solvent having a boiling point of 85° C. or lower. If the amount of hydrogen peroxide is greater than 30% by mass, an excessive amount of hydrogen peroxide remains after molding of the bottle. A conventionally commonly used sterilizer is a hydrogen peroxide solution containing 35% by mass of hydrogen peroxide. According to the present invention, the sterilizer contains the solvent having a boiling point of 85° C. or less as a constituent, the sterilizer has a lower condensation temperature when the sterilizer is in the form of gas and forms a finer mist when the sterilizer condenses. Therefore, the effect of sterilization of the sterilizer gas G and the mist of the condensate of the sterilizer on the surface of the preform 1 is improved, so that a sufficient sterilization effect can be achieved with the reduced content of hydrogen peroxide in the sterilizer.

Since the sterilizer at least contains 30% by mass or less of hydrogen peroxide and a solvent having a boiling point of 85° C. or lower, compared with the conventional sterilizer containing only hydrogen peroxide and water, the angle of contact of a drop of the mist of the sterilizer formed on the surface of the preform 1 after the sterilizer gas G is blasted to the preform 1 is small. Therefore, even a drop of the same mass has a larger coverage area and is expected to have a higher sterilization effect when the hydrogen peroxide in the drop decomposes.

A more preferable range of the content of hydrogen peroxide in the sterilizer is from 0.5% by mass to 30% by mass. If the content is less than 0.5% by mass, the sterilizing power may be insufficient. Since the content is equal to or less than 30% by mass, the amount of the remaining hydrogen peroxide can be further reduced. Furthermore, the content of hydrogen peroxide is more preferably equal to or less than 20% by mass. Depending on the kind or amount of the solvent having a boiling point of 85° C. or lower, the amount of the remaining hydrogen peroxide can be further reduced.

The solvent having a boiling point of 85° C. or lower is methyl alcohol, ethyl alcohol, isopropyl alcohol or acetone, for example. The solvent may contain only one of these materials or a mixture of two or more of these materials. The other constituent of the sterilizer than hydrogen peroxide and the solvent having a boiling point of 85° C. or lower is water. These constituents have to form a uniform composition when mixed. The solvent having a boiling point of 85° C. or lower is particularly preferably ethyl alcohol from the viewpoint of safety.

The sterilizer is optically a solution containing 0.5% by mass to 30% by mass of hydrogen peroxide and 14% by mass to 99% by mass of ethyl alcohol. If the content of ethyl alcohol is less than 14% by mass, the amount of the remaining hydrogen peroxide cannot be sufficiently reduced.

As shown in FIG. 4, the sterilizer is gasified by a sterilizer gas generator 7. The sterilizer gas generator 7 is provided with a sterilizer supplying portion 8 that is a twin-fluid spray nozzle for supplying the sterilizer in the form of liquid drops and an evaporating portion 9 for evaporating the sterilizer supplied from the sterilizer supplying portion 8 by heating the sterilizer to a temperature equal to or lower than the decomposition temperature of hydrogen peroxide. The sterilizer supplying portion 8 is configured to take in the sterilizer from a sterilizer supply path 8a and compressed air from a compressed air supply path 8b and then sprays the sterilizer into the evaporating portion 9. The evaporating portion 9 is a pipe with a heater 9a interposed between inner and outer walls thereof, and the sterilizer blasted into the pipe is heated and evaporated. The evaporated sterilizer gas is jetted out of the evaporating portion 9 through the sterilizer gas blasting nozzle 6. Instead of using the heater 9a, the evaporating portion 9 may be heated by dielectric heating.

With regard to operational conditions of the sterilizer supplying portion 8, the pressure of the compressed air is adjusted to fall within a range from 0.05 MPa to 0.6 MPa, for example. The sterilizer may be supplied by gravity or under pressure. The inner surface of the evaporating portion 9 is heated to 140° C. to 450° C. to evaporate the sprayed sterilizer.

As shown in FIG. 2(A), the sterilizer gas G is blasted from the sterilizer gas blasting nozzle 6 to the preform 1 (the sterilizer gas blasting step).

Figure 5:
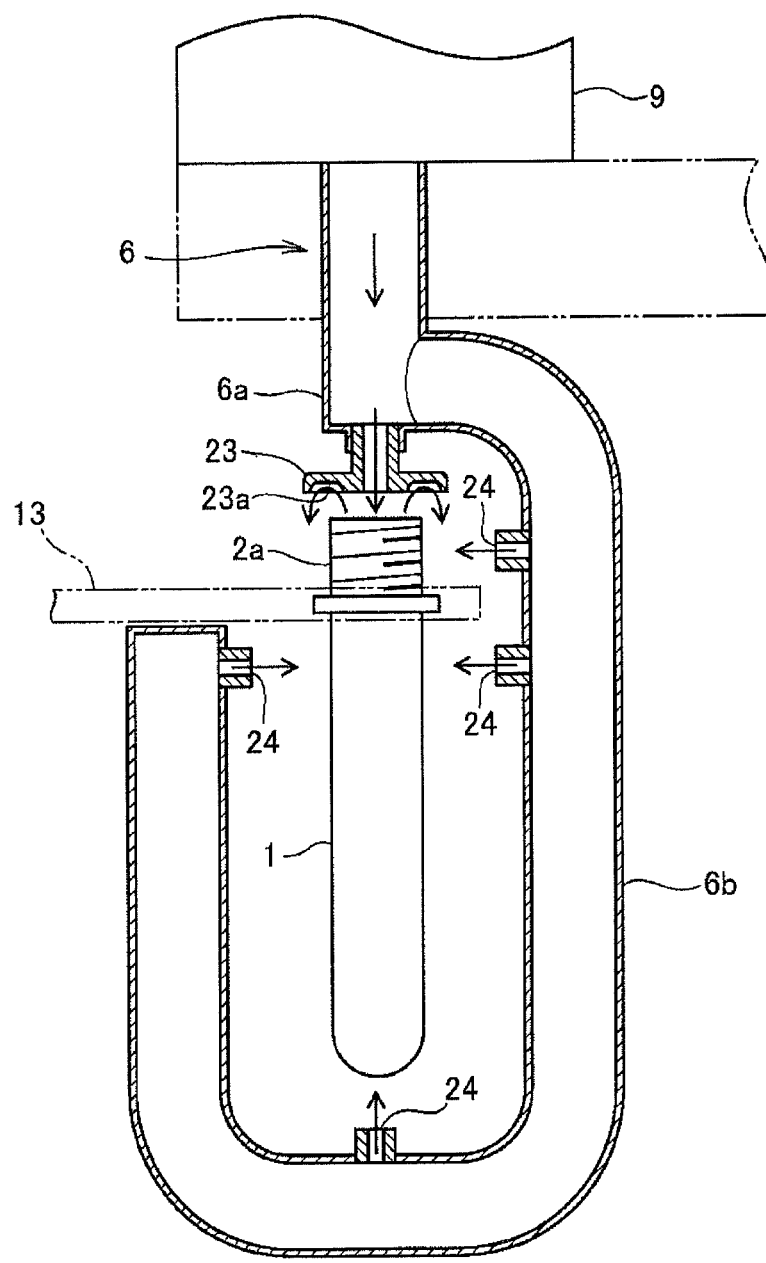
FIG. 5 is a vertical cross-sectional view of a sterilizer gas blasting nozzle incorporated in the apparatus for sterilizing a preform according to the present invention.

When the sterilizer gas G is blasted from the sterilizer gas blasting nozzle 6 to the preform 1, as shown in FIG. 5, the sterilizer gas G may be divided into two flows in the sterilizer gas blasting nozzle 6, one of the flows being blasted into the preform 1 from a nozzle 6a and the other being blasted to an outer surface of the preform 1 from a sterilizer gas blasting port 24 of a nozzle 6b. After the sterilizer gas G exits the sterilizer gas blasting nozzle 6, the sterilizer gas G flows into the preform 1 or is blasted to the outer surface of the preform 1 in the form of gas, mist of the condensate of the sterilizer gas G, or a mixture thereof.

Hot air that is aseptic air may be supplied to a middle of the sterilizer gas blasting nozzle 6 and the nozzles 6a and 6b to prevent condensation of the sterilizer containing hydrogen peroxide on the nozzles 6a and 6b. Alternatively, an electric ribbon heater may be wound around the nozzles 6a and 6b or other components to prevent condensation of the sterilizer.

The flow of the sterilizer gas G jetted into the preform 1 is covered by an umbrella-shaped member 23. Although the sterilizer gas G or mist flowing into the preform 1 spills from the mouth portion 2a of the preform 1, the flow of the spilling sterilizer gas G or the like collides with the umbrella-shaped member 23 and changes direction towards the outer surface of the preform 1 by being guided by an annular groove 23a formed in an inner surface of the umbrella-shaped member 23, so that the flow of the sterilizer gas G can be blasted to the outer surface of the preform 1.

By blasting the sterilizer gas G or mist or a mixture thereof to the inner and outer surfaces of the preform 1, bacteria on the surface of the preform 1 is killed or damaged.

Immediately before the blasting of the sterilizer gas G to the preform 1 shown in FIG. 2(A), the preform 1 may be preliminarily heated by blasting heated air to the preform 1. The preliminary heating can further improve the sterilization effect on the preform 1.

Instead of providing only sterilizer gas blasting nozzle 6, a plurality of sterilizer gas blasting nozzles 6 may be arranged along the traveling path of the preform 1, and the sterilizer gas G may be blasted to the preform 1 from the sterilizer gas blasting nozzles 6.

The preform 1 to which the sterilizer gas has been blasted may be grasped by the gripper 13 as shown in FIG. 2(B), and the air P may be blasted to the preform 1 from the air nozzle 37 while the preform 1 is being conveyed.

The blasted air P activates the hydrogen peroxide on the surface of the preform 1, and the activated hydrogen peroxide kills the bacteria on the inner and outer surfaces of the preform 1. In addition, by blasting the air P, the sterilizer on the preform 1 is quickly removed from the surface of the preform 1. Since the sterilizer on the preform 1 is removed from the preform 1 by the blasting of the air P before the preform 1 enters the heating furnace 25, various devices such as a seal member in the blow-molding machine 12 are prevented from being damaged by hydrogen peroxide. In addition, whitening, distortion, uneven molding or other defects of the bottle due to the sterilizer on the preform 1 can be prevented.

The air P can be at room temperature. However, hot air P, which is the air P heated, promotes decomposition of hydrogen peroxide to improve the sterilization effect and reduces the amount of the remaining hydrogen peroxide. The air P is desirably heated in such a manner that the temperature of the air P is 40° C. to 140° C. when the air P is blasted to the preform. If the temperature is lower than 40° C., the sterilization effect is insufficient, and if the temperature is higher than 140° C., the air P causes deformation or other defects of the mouth portion 2a of the preform 1. For this reason, the temperature is preferably 40° C. to 140° C.

As shown in FIG. 2(B), the air P is blasted through a slit-shaped air blasting port 37a formed in a box-shaped manifold 37b that is the main body of the air nozzle 37.

Figure 6:
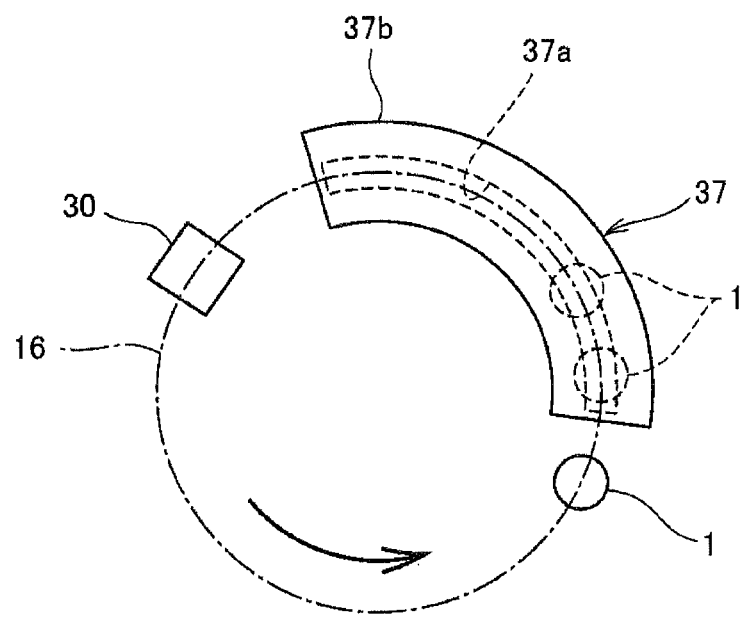
FIGS. 6(A) and 6(B) show an air nozzle incorporated in the apparatus for sterilizing a preform according to the present invention.
Figure 6:
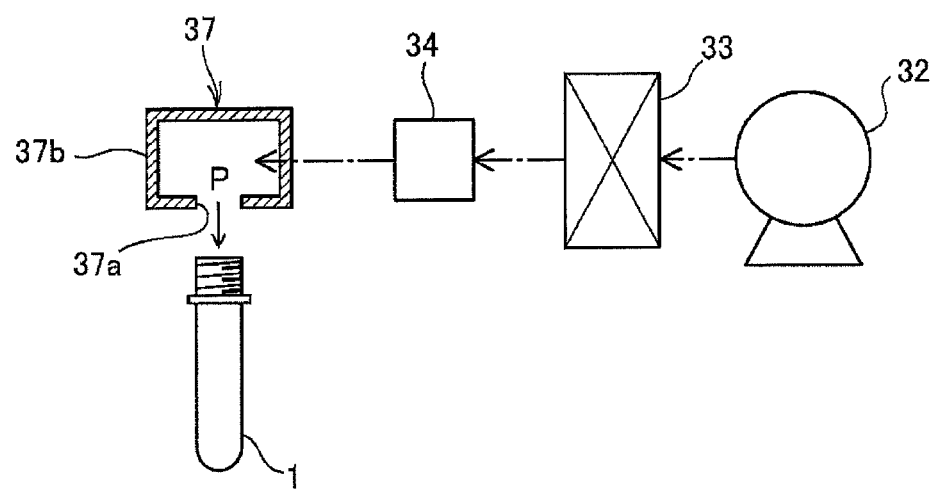

Furthermore, as shown in FIG. 6(A), the box-shaped manifold 37b of the air nozzle 37 is curved along the arc of the wheel 16, and the slit-shaped air blasting port 37a is formed in a bottom surface of the manifold 37b. The air nozzle 37 is arranged on the wheel 16 in such a manner that the air blasting port 37a extends along the traveling path of the preform 1 on the wheel 16. In addition, as shown in FIG. 6(B), a blower 32, a sterilizing filter 33 and an electric heater 34 are connected to the manifold 37b. Outside air taken in by the blower 32 is sterilized by the sterilizing filter 33 and heated by the electric heater 34, and the resulting hot air P is fed into the air nozzle 37.

The air supplied to the air nozzle 37 may not be the air from the blower 32 but may be compressed air having higher driving force sterilized by an aseptic filter. Alternatively, high-pressure air used for blow molding in the blow-molding machine 12 may be collected and reused.

As shown in FIG. 6(B), the air P supplied into the manifold 37b of the air nozzle 37 jets from the air blasting port 37a and is blasted to the preform 1 traveling below the air blasting port 37a with the mouth portion 2a facing up, and some of the air P flows into the preform 1, and other of the air P flows along the outer surface of the preform 1.

Figure 7:
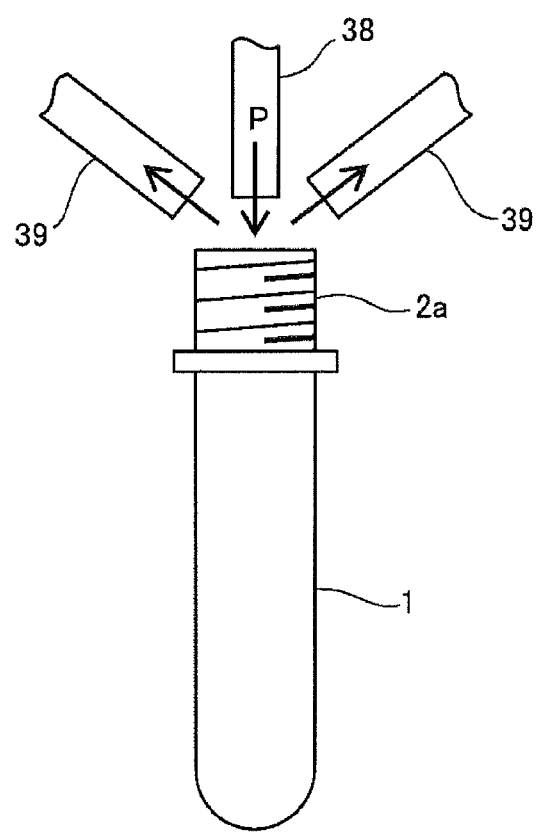
FIG. 7 is a diagram for illustrating a modification of a step of blasting air to the preform.

As shown in FIG. 7, sterilized air P may be blasted to the preform 1 from a tubular air blasting nozzle 38. Furthermore, a suction tube 39 may be arranged near the air blasting nozzle 38 to suck a foreign matter such as dust discharged from the preform 1 when the air P is blasted into the preform 1 from the air blasting nozzle 38. By the suction tube 39 collecting foreign matters in this way, a foreign matter can be prevented from entering another preform 1 or the bottle 2 molded therefrom.

Figure 8:
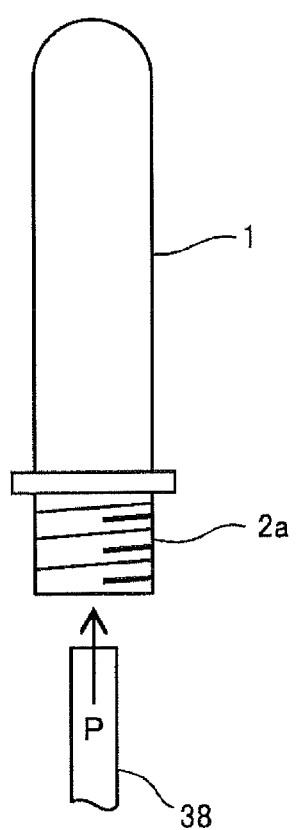
FIG. 8 is a diagram for illustrating another modification of the step of blasting air to the preform.

Furthermore, as shown in FIG. 8, the air blasting nozzle 38 may be arranged to face up, the preform 1 may be arranged in the inverted position, and sterilized air P may be blasted from the air blasting nozzle 38 into the mouth portion 2a of the preform 1 facing down. With such an arrangement, foreign matters in the preform 1 drop off the preform 1 under the pressure of the air blasted from the air blasting nozzle 38 and under their own weight.

Figure 9:
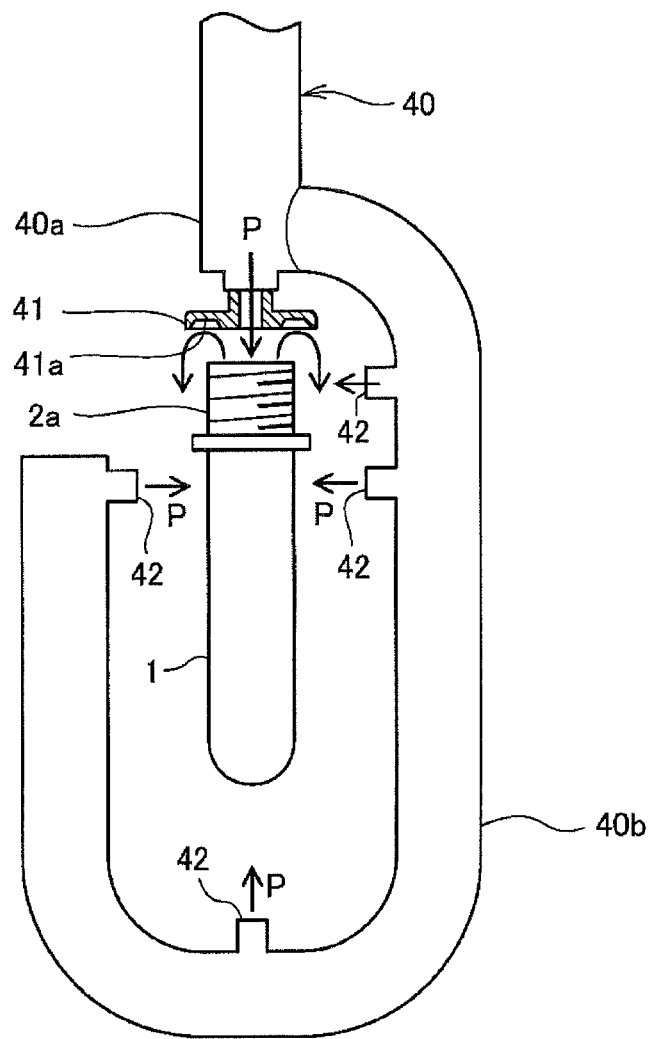
FIG. 9 is a diagram for illustrating another modification of the step of blasting air to the preform.

Air P may be supplied from an air nozzle 40 shown in FIG. 9. The air nozzle 40 has the same configuration as the sterilizer gas blasting nozzle 6 shown in FIG. 5. In FIG. 9, nozzles 40a and 40b are a plurality of branch nozzles for feeding the air P. Of the plurality of nozzles 40a and 40b, a blasting port of one nozzle 40a is opposed to the opening of the mouth portion 2a of the preform 1. The air P is blasted to the preform 1 from the blasting port of the nozzle 40a and flows into the preform 1. In this way, the hydrogen peroxide on the inner surface of the preform 1 is activated, and any excessive hydrogen peroxide is removed.

An umbrella-shaped member 41 is a member that covers the blasting port of the nozzle 40a. An annular groove 41a having a substantially semicircular cross section is formed in a lower surface of the umbrella-shaped member 41. The air P entering in the preform 1 from the blasting port of the nozzle 40a fills the interior of the preform 1 and then spills from the mouth portion 2a of the preform 1. The spilt air P is guided to the outer surface of the preform 1 by the lower surface of the umbrella-shaped member 41 and the annular groove 41a, and then flows along the outer surface of the preform 1. In this way, the air P from the nozzle 40a eventually comes into contact with the outer surface of the preform 1.

The other nozzle 40b having a substantially U-shape extends in conformity with the outer surface of the preform 1, and a blasting port 42 of the nozzle 40b is opposed to the outer surface of the preform 1. Air P is blasted from the blasting port 42 of the nozzle 40b to the outer surface of the preform 1 and comes into contact with the outer surface of the preform 1. In this way, both the air P from the nozzle 40b and the air P spilt from the mouth portion 2a of the preform 1 activate the hydrogen peroxide on the outer surface of the preform 1 and remove any excessive hydrogen peroxide.

After the blasting of the air P is completed, the preform 1 may be irradiated with the light L containing ultraviolet rays as shown in FIG. 2(C) (the light irradiation step). This step may be performed before or after the blasting of the sterilizer gas G. At least the mouth portion of the preform 1 may be irradiated with an electron beam instead of the light L containing ultraviolet rays.

The ultraviolet rays described above is a kind of electromagnetic wave having a wavelength of 100 nm to 380 nm. The light L includes a component having any wavelength in this range. In particular, ultraviolet rays having a wavelength of 100 nm to 280 nm, which is referred to as UV-C, is effective for sterilization. Ultraviolet rays having a wavelength of 253.7 nm has the highest sterilization effect, and the light L most preferably includes the ultraviolet rays.

The light irradiation apparatus 30 that emits ultraviolet rays having a wavelength from 100 nm to 380 nm includes a low-pressure mercury lamp, a high-pressure mercury lamp, or a xenon flash lamp, for example. Light (having a wavelength of 100 to 950 nm) emitted from the xenon flash lamp containing xenon gas therein has a particularly high sterilization effect, so that the irradiation apparatus most preferably has the xenon flash lamp.

The sterilization effect of light is proportional to the amount of irradiation per unit area and the duration of irradiation. The light emitted from the xenon flash lamp has a higher sterilization effect than the light emitted from the low-pressure mercury lamp or high-pressure mercury lamp and therefore can sufficiently sterilize the preform 1 in a shorter time. Therefore, a rise in temperature of the preform 1 can be prevented.

A reflector plate 31 shown in FIG. 2(C) is disposed in order to efficiently irradiate the preform 1 with the light L emitted from the lamp 30a. Therefore, the reflector plate 31 is arranged on the side of the lamp 30a opposite to the preform 1. The reflector plate 31 may be formed by any combination of a plurality of flat or curved surfaces of any shape. Any reflector plate 31 can be used as far as the reflector plate 31 can reflect the light L. For example, the reflector plate may be made of a resin or a metal and may have a smooth surface, which may be formed by coating, plating with a metal, vapor deposition of a metal or a metal oxide, or a combination thereof.

As shown in FIG. 2(C), the mouth portion 2a is not the only part of the preform 1 irradiated with the light L, and any part of the preform 1 can be irradiated with the light L. The irradiation with the light L promotes sterilization of the irradiated part.

If the mouth portion 2a is deformed by heating, the aseptic condition of the product filled with the content shown in FIG. 3(H) is compromised. To avoid this, when the hot air P is used, the amount of the hot air P blasted to the outer surface is reduced, or the temperature in the heating furnace 25 during heating for blow molding is reduced, for example. This may lead to insufficient sterilization of the mouth portion 2a. Such poor sterilization of the mouth portion 2a can be avoided by concentrating the irradiation with the light L to the mouth portion 2a, thereby effectively sterilizing the mouth portion 2a.

In this case, like the light irradiation apparatus 30 shown in FIG. 2(C), it is particularly preferably to arrange the lamp 30a above the mouth portion 2a and arrange the reflector plate 31 to surround the lamp 30a. With such an arrangement, the inner and outer surfaces of the mouth portion 2a can be efficiently irradiated with the light L.

The preform 1 is then conveyed into the heating furnace by the heating furnace conveying wheel 17, and as shown in FIG. 2(D), the preform 1 is heated to a temperature suitable for the subsequent blow molding by the infrared heater 18a or other heating device. As shown in FIG. 2(D), the spindle 29 is inserted into the mouth portion 2a of the preform 1, so that the preform 1 suspended in the upright position (or inverted position) and rotating with the spindle 29 is conveyed into the heating furnace 25 by an endless chain 18. Spindles 29 are attached to the endless chain 18 at regular intervals. The spindle 29 is capable of rotating, and the endless chain 18 is rotated by pulleys 26a and 26b. The hydrogen peroxide remaining on the preform 1 may be further decomposed by this heating, and sterilization of the preform 1 may be further promoted. As a result, the amount of the remaining hydrogen peroxide may be further reduced.

Figure 10:
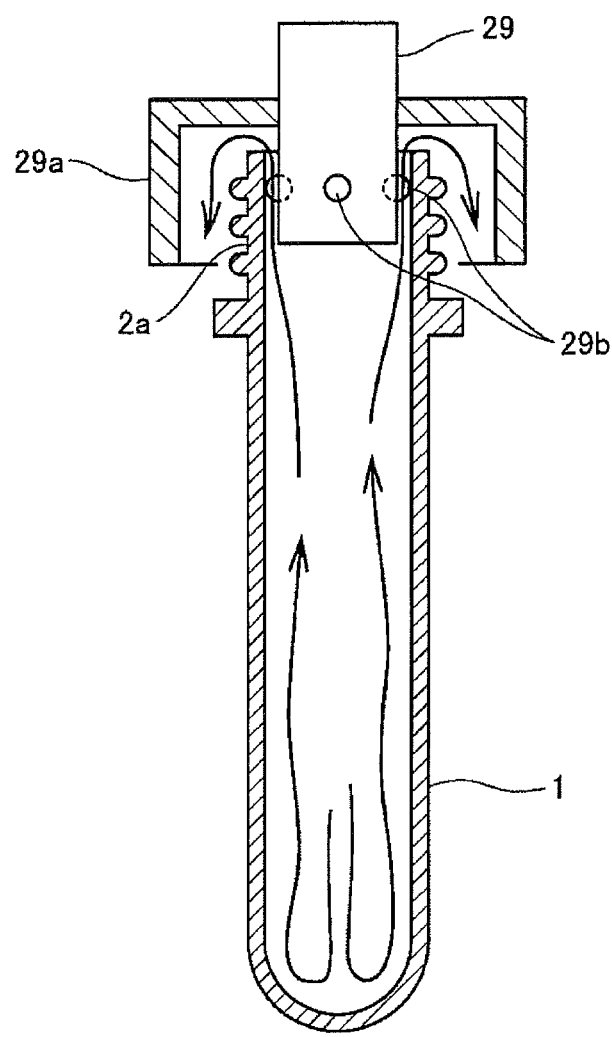
FIG. 10 is a diagram for illustrating a modification of a step of heating the preform to a molding temperature.

As shown in FIG. 10, when a lower part of the spindle 29 is inserted into the mouth portion 2a of the preform 1, an elastic body 29b is elastically deformed, and thereby the preform 1 is supported on the spindle 29. At the same time, if there is an umbrella-shaped member 29a, the mouth portion 2a of the preform 1 is covered by the umbrella-shaped member 29a.

In this case, a gap is formed between the inner surface of the mouth portion 2a of the preform 1 and the lower part of the spindle 29 and between the outer surface of the mouth portion 2a of the preform 1 and the umbrella-shaped member 29a, so that hot air, which is the air in the preform 1 heated by heat from the infrared heater 18a, flows from inside the preform 1 to outside of the preform 1 through the gap and at the same time heats the mouth portion 2a of the preform 1.

Considerations have to be made to prevent the mouth portion 2a of the preform 1 from being deformed by the heat applied before the preform 1 is molded into the bottle 2, in order to compromise the sealing of the bottle 2 with the cap 3 after the preform 1 is molded into the bottle 2.

The hot air flowing in the gap described above heats the mouth portion 2a to a temperature equal to or lower than 70° C., at which the mouth portion 2a is not deformed. The heating of the mouth portion 2a may activate the trace amount of hydrogen peroxide remaining on the mouth portion 2a, and the mouth portion 2a may be appropriately sterilized.

Figure 11:
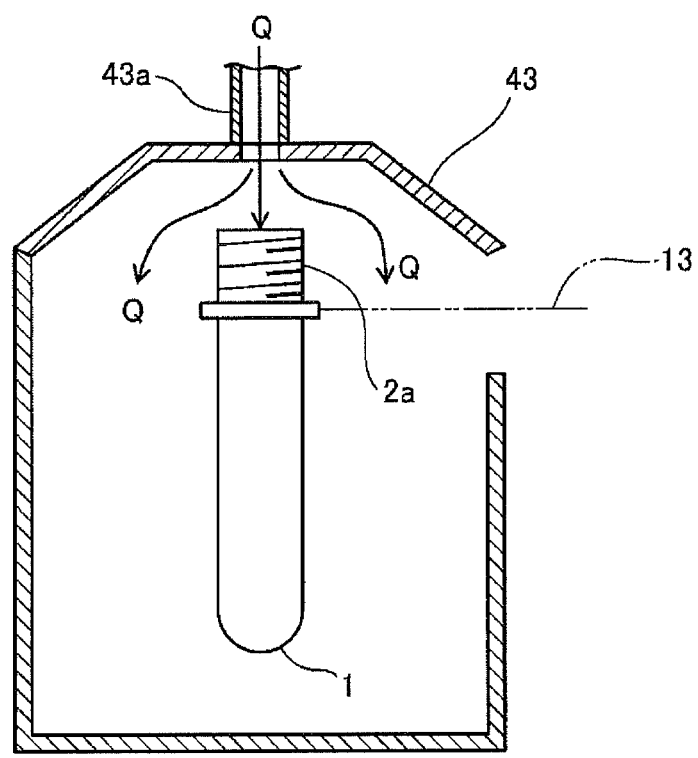
FIG. 11 is a diagram for illustrating a modification of a step following the step of heating the preform to the molding temperature.

As shown in FIG. 11, the heated preform 1 may be released from the spindle 29, passed to the gripper 13, and conveyed to the mold 4, which is a blow-molding die, shown in FIG. 3(E) while aseptic air Q is blasted to the preform 1 from the side of the mouth portion 2a thereof. The preform 1 is fed to the mold 4 while the aseptic condition thereof is maintained by the blasting of the aseptic air Q.

The aseptic air Q described above may be hot air. By blasting hot air, the temperature of the preform 1 is prevented from lowering.

As shown in FIG. 11, at a location where the heating of the preform 1 is completed and the preform 1 is passed to the mold 4, a tunnel-shaped cover 43 may be provided to surround the traveling path of the preform 1. A ceiling portion of the tunnel-shaped cover 43 that covers the mouth portion 2a of the preform 1 from above has the shape of a roof having an inclined surface. A row of pipe-shaped nozzles 43a or a slit-shaped nozzle 43a is provided in the ceiling portion for blasting the aseptic air Q to the mouth portion 2a of the preform 1. Thus, the aseptic air Q is efficiently supplied to the preform 1, and the preform 1 travels in the chamber 28b with the aseptic condition thereof maintained. If the molding machine is provided in an aseptic chamber, the tunnel-shaped cover 43 is unnecessary.

As shown in FIG. 3(E), the heated preform 1 is blow-molded into the bottle 2 in the mold 4. The mold 4, which is a blow-molding die, is clamped while continuously traveling at the same traveling speed as the preform 1, and then is opened after the preform 1 is blow-molded in the mold 4. Upon the preform 1 being set in the mold 4 and an extension rod being inserted into the preform 1 through a central hole of the blow nozzle 5, blow air is blasted into the preform 1. The blow air must be aseptic air from which bacteria have been removed by a sterilizing filter or the like. The preform 1 is expanded by the extension rod and blow air into the shape of the mold 4 to form the bottle 2. The bottle 2 is grasped by the gripper 13 and conveyed to the inspection apparatus 27 by the wheel 21.

Although not shown, the inspection apparatus 27 can be provided with a light source and a camera for inspecting whether the top surface of the mouth portion 2a of the molded bottle 2 is smooth or not, for example.

If the inspected bottle 2 is defective, the bottle 2 is removed from the conveying path by a removing apparatus (not shown). Only the bottles 2 that are not determined to be defective are conveyed to the wheel 22.

The bottle 2 that is not determined to be defective is conveyed to the filling apparatus by the wheel 22.

As shown in FIG. 1, the wheels 15 and 16 are surrounded by the chamber 28a. An exhaust device formed by a filter 36 that filters air in the chamber 28a and a blower 35 is connected to the chamber 28a. Any excessive sterilizer gas blasted from the sterilizer gas blasting nozzle 6 is removed by the filter 36 of the exhaust device and discharged to the outside of the chamber 28a. Therefore, the hydrogen peroxide in the sterilizer can be prevented from flowing into the adjacent heating furnace 25 or blow-molding machine 12. The amount of air supplied to or discharged from the chamber 28a is desirably adjusted so that the pressure in the chamber 28a is a negative pressure lower than the atmospheric pressure.

As shown in FIG. 1, the heating furnace 25 and the blow-molding machine 12 are surrounded by the chamber 28b. The pressure in the chamber 28b is desirably adjusted to be a positive pressure by supplying aseptic air. The aseptic air can be obtained by sterilizing air from a blower through a sterilizing filter.

As shown in FIG. 1, the wheel 22 is surrounded by a chamber 28c. Aseptic air is desirably also supplied to the chamber 28c. The pressure in the chamber 28c is desirably adjusted to be between the pressure of the aseptic air supplied to the filling section where the bottle 2 is filled with the content in the subsequent step and the pressure in the chamber 28b.

By maintaining the interior of the chambers 28b and 28c at a positive pressure by supplying aseptic air, bacteria can be prevented from entering the chambers from outside, and the aseptic condition in the chambers that is achieved by sterilization before operation can be maintained. The sterilization before operation may be gas sterilization of the interior of the chambers 28a, 28b and 28c by a hydrogen peroxide gas having a concentration of 10 mg/L or less, for example. Alternatively, portions of the chambers that are to come into contact with the preform 1 or the bottle 2 may be irradiated with light containing ultraviolet rays. Alternatively, a chemical containing 1% by mass of ethanol or hydrogen peroxide may be sprayed to portions that are to come into contact with the preform 1 or the bottle 2, such as the mold 4, the blow nozzle 5 and the gripper 13.

Examples

In the following, the first embodiment of the present invention will be described with regard to examples.

(Method of Operation)

A preform 1 having a weight of 20 g that is intended for a 500 ml bottle made of polyethylene terephthalate was used. $10^3$, $10^4$ and $10^5$ B. atrophaeus spores were put on the inner surface of the preform 1 at a total of nine points including three points in the mouth portion, three points in a middle portion of the body, and three points in a bottom portion and air-dried, thereby providing a bacteria-contaminated preform 1.

Then, the light irradiation apparatus 30 provided with the lamp 30a and the dome-shaped reflector plate 31 surrounding the lamp 30a as shown in FIG. 2(C) was used to intensively irradiate the inner and outer surfaces of the mouth portion 2a of the preform 1 with the light L. The lamp was a xenon lamp (having an arc length of 500 nm) available from Econos Japan Co. Ltd., and a pulse of 0.2 sec/time was irradiated six times (the light irradiation step).

Then, the sterilizer gas G was blasted to the bacteria-contaminated preform 1 from the sterilizer gas blasting nozzle 6 shown in FIG. 2(A). The sterilizer gas G was generated by supplying compressed air having a pressure of 0.5 MPa and the sterilizer at a flowrate of 10 to 60 ml/min to the sterilizer gas generator 7 shown in FIG. 4. The surface temperature of the evaporating portion 9 was set at 300° C. The resulting sterilizer gas G was blasted to the preform 1 (the sterilizer gas blasting step).

Furthermore, air was blasted to the preform 1 from the air blasting port 37a of the air nozzle 37 shown in FIG. 2(B) at a flowrate of 600 L/min for 1.2 seconds. At the same time, the air P was heated to 70° C.

Then, as shown in FIG. 2(D), the preform 1 was heated in the heating furnace 25 until the temperature of the outer surface of the body portion of the preform 1 reaches 120° C. Furthermore, as shown in FIG. 3(E), the preform 1 was molded in the mold 4 into a 500 ml bottle.

(Method of Measuring Sterilization Effect)

The molded bottle 2 was filled with 100 ml of SCD bouillon medium in an aseptic atmosphere and sealed with an aseptic cap 3. After that, the bottle was shaken to make the medium come into contact with the whole of the inner surface of the bottle 2, and cultivation was performed at 35° C. for one week. If the medium became opaque, the sterilization was determined to be insufficient. If the medium did not become opaque, the sterilization was determined to be sufficient.

(Method of Measuring Amount of Hydrogen Peroxide Remaining in Bottle)

The molded bottle 2 was filled with 500 ml of pure water and sealed. After that, the concentration of hydrogen peroxide in the pure water was measured by SUPER ORITECTOR MODEL5 available from Chiyoda Manufacturing Co. Ltd.

Examples, Comparative Examples and Results

Table 1 shows examples and comparative examples in which the same operation as that described in Method of Operation was performed. Table 1 shows operational conditions of the examples and comparative examples such as the composition of the sterilizer, the presence or absence of heating of air, and the presence or absence of irradiation with light containing ultraviolet rays, the sterilization effect, and the amount of hydrogen peroxide remaining in the bottle 2.

TABLE 1

| | COMPOSITION OF STERILIZER (% BY MASS) | | | BLASTING OF AIR | LIGHT IRRADIATION | STERILIZATION EFFECT | REMAINING HYDROGEN PEROXIDE (ppm) |
| --- | --- | --- | --- | --- | --- | --- | --- |
| | HYDROGEN PEROXIDE | ETHANOL | WATER | | | | |
| EXAMPLE 1 | 30 | 14 | 56 | HOT | PRESENCE | ○ | 0.04 |
| EXAMPLE 2 | 20 | 43 | 37 | HOT | PRESENCE | ○ | 0.02 |
| EXAMPLE 3 | 15 | 57 | 28 | HOT | PRESENCE | ○ | 0.01 |
| EXAMPLE 4 | 10 | 71 | 19 | HOT | PRESENCE | ○ | 0.01 |
| EXAMPLE 5 | 10 | 71 | 19 | ROOM TEMPERATURE | PRESENCE | ○ | 0.03 |
| EXAMPLE 6 | 5 | 85 | 9 | HOT | PRESENCE | ○ | <0.01 |
| EXAMPLE 7 | 5 | 85 | 9 | ROOM TEMPERATURE | PRESENCE | ○ | 0.02 |
| EXAMPLE 8 | 1 | 93 | 2 | HOT | PRESENCE | ○ | <0.01 |
| EXAMPLE 9 | 1 | 93 | 2 | ROOM TEMPERATURE | PRESENCE | ○ | 0.01 |
| COMPARATIVE EXAMPLE 1 | 35 | 0 | 65 | HOT | PRESENCE | ○ | 0.08 |
| COMPARATIVE EXAMPLE 2 | 20 | 0 | 80 | HOT | ABSENCE | x | 0.04 |
| COMPARATIVE EXAMPLE 3 | 15 | 0 | 85 | HOT | PRESENCE | x | 0.04 |
| COMPARATIVE EXAMPLE 4 | 0 | 100 | 0 | HOT | PRESENCE | x | <0.01 |

In the table, a circle represents that the sterilization was determined to be perfect in the measurement of sterilization effect.

According to the examples described above, when a sterilizer containing 30% by mass or less of hydrogen peroxide and ethanol having a boiling point of 85° C. or lower as a solvent is used, the preform 1 can be sufficiently sterilized, and the amount of the hydrogen peroxide remaining in the bottle 2 molded from the preform 1 can be reduced. If the content of hydrogen peroxide is greater than 30% by mass, the sterilization can be sufficiently achieved, but the amount of the remaining hydrogen peroxide is high even if the sterilizer does not contain ethanol. If the content of hydrogen peroxide is equal to or less than 30% by mass, the sterilization is insufficient if the sterilizer contains no ethanol. Under conditions that the content of hydrogen peroxide is equal to or less than 5% by mass, the sterilizer contains ethanol, and air at room temperature is blasted, the preform 1 can be sufficiently sterilized, and the amount of the hydrogen peroxide remaining in the bottle 2 molded from the preform 1 can be reduced.

In the following, a second embodiment of the present invention will be described with reference to the drawings.

Second Embodiment

The second embodiment of the present invention differs from the first embodiment in that after the sterilizer gas blasting step, air is not blasted to the preform 1, and the heating step is performed. According to the second embodiment, an aseptic preform can be simply obtained by sterilizing the preform, and the amount of the hydrogen peroxide remaining on the bottle molded from the preform can be reduced.

(Overview of Method and Apparatus)

Figure 12:
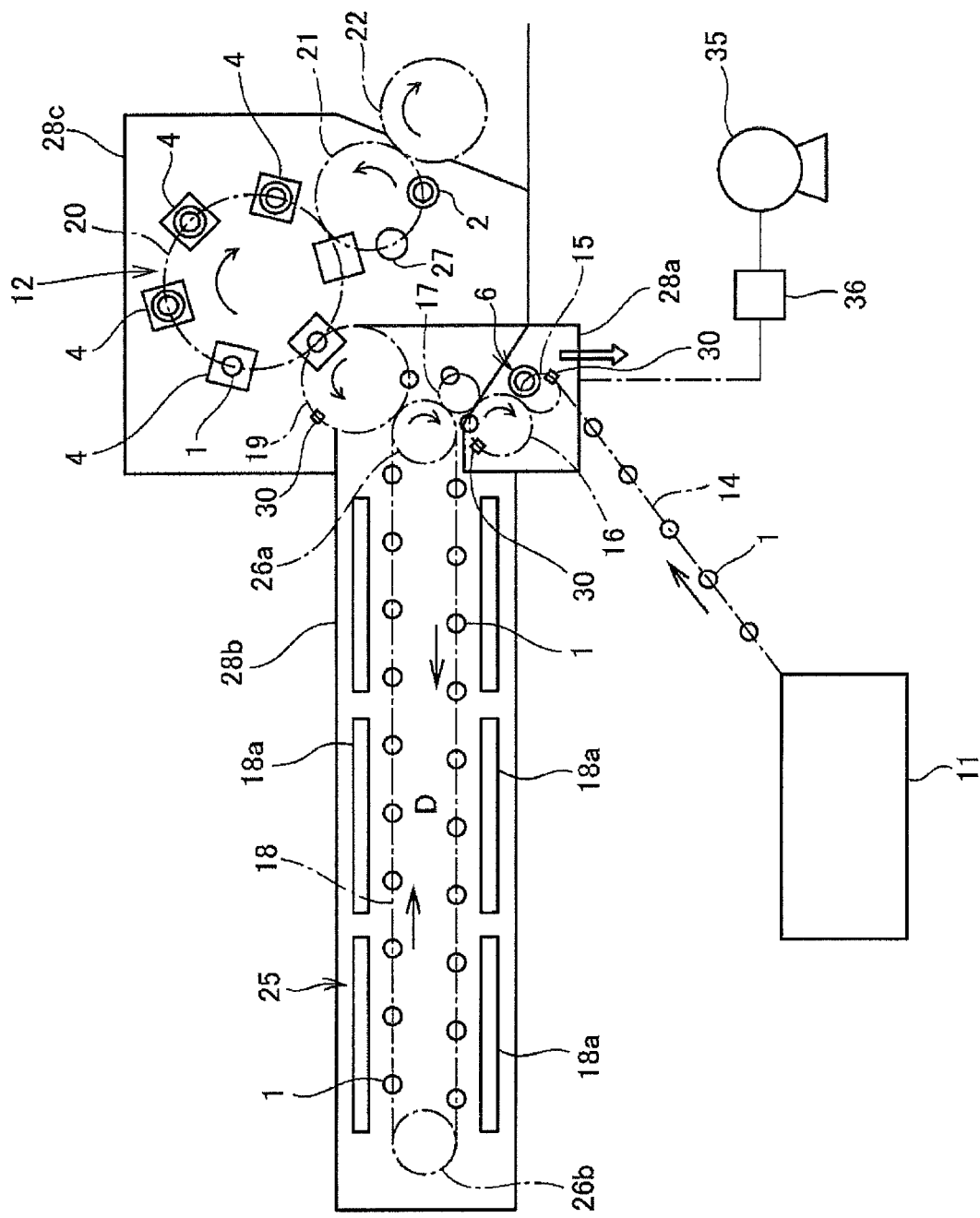
FIG. 12 is a schematic plan view of an aseptic filling system incorporating an apparatus for sterilizing a preform according to the present invention illustrating a process up to molding of the preform into a bottle.

As shown in FIG. 12, the preform 1 is fed from the preform feeding apparatus 11 and conveyed into the sterilizer blasting chamber 28*a* by the preform feeding conveyor 14.

The preform 1 is passed to the sterilizer gas blasting wheel 15, and as shown in FIG. 2(C), the preform 1 is irradiated with light L containing ultraviolet rays emitted by the lamp 30*a* incorporated in the light irradiation apparatus 30 (light irradiation step). The light irradiation step is the same as that in the first embodiment.

Although the blasting of the sterilizer gas G to the preform 1 (the sterilizer gas blasting step) is essential, the irradiation with light (the light irradiation step) is optional. Although the blasting of the sterilizer gas G to the preform 1 (the sterilizer gas blasting step) and the heating of the preform 1 to a temperature for molding the preform 1 into the bottle 2 (the heating step) are performed in this order, the irradiation of the preform 1 with light (the light irradiation step) can be performed at any time.

That is, the light irradiation apparatus 30 may be disposed upstream of the nozzle 6 along the sterilizer gas blasting wheel 15, or along the wheel 16 following the sterilizer gas blasting wheel 15. Alternatively, the light irradiation apparatus 30 may be disposed along the wheel 19 to which the preform 1 is conveyed after heated. Furthermore, a plurality of light irradiation apparatuses 30 may be arranged at a plurality of these three locations.

The preform 1 to which the sterilizer gas has been blasted passes through the heating furnace conveying wheel 17, is released from the gripper 13 that has grasped the preform 1 being conveyed by the wheel 17, and conveyed into the heating furnace 25.

The preform 1 having entered the heating furnace 25 is heated by the infrared heater 18*a* or other heating device to a temperature suitable for the subsequent blow-molding, as shown in FIG. 2(D) (the heating step). The temperature is about 90° C. to 130° C. The sterilizer having been blasted to the preform 1 is activated by heating (in the heating step) to kill bacteria or the like on the surface of the preform 1. In addition, an excessive sterilizer is volatilized by heating.

A mouth portion 2*a* of the preform 1 is kept at a temperature equal to or less than 70° C. for preventing deformation or the like.

The heating step for the preform 1, the blow molding of the heated preform into the bottle 2, the inspection of the molded bottle 2, the filling of the inspected bottle 2 with the content, and the sealing of the filled bottle 2 are the same as those in the first embodiment.

(Details of Method and Apparatus)

The preform 1 and the sterilizer according to the second embodiment of present invention are the same as those in the first embodiment. The sterilizer gas is generated by the sterilizer gas generator shown in FIG. 4 in the same manner as in the first embodiment.

As shown in FIG. 2(A), the sterilizer gas is blasted from the sterilizer gas blasting nozzle 6 to the preform 1 (the sterilizer gas blasting step). The blasting of the sterilizer gas to the preform 1 is also the same as that in the first embodiment. Immediately before the blasting of the sterilizer gas to the preform 1 shown in FIG. 2(A), the preform 1 may be preliminarily heated by blasting heated air to the preform 1, for example. The preliminary heating can further improve the sterilization effect on the preform 1.

Before the blasting of the sterilizer gas to the preform 1, at least the mouth portion 2a of the preform 1 may be irradiated with light containing ultraviolet rays as shown in FIG. 2(C) (the light irradiation step). This step may be performed after the blasting of the sterilizer gas. At least the mouth portion of the preform 1 may be irradiated with an electron beam instead of the light containing ultraviolet rays. The light containing ultraviolet rays and the light irradiation apparatus 30 that emits the light are the same as those in the first embodiment.

As shown in FIG. 2(C), the mouth portion 2a is not the only part of the preform 1 irradiated with light, and any part of the preform 1 can be irradiated with light. The irradiation with light promotes sterilization of the irradiated part.

If the mouth portion 2a is deformed by heating, the aseptic condition of the product filled with the content shown in FIG. 3(H) is compromised. To avoid this, the temperature in the heating furnace 25 during heating for blow molding is reduced. This may lead to insufficient sterilization of the mouth portion 2a. Such poor sterilization of the mouth portion 2a can be avoided by concentrating the irradiation with light to the mouth portion 2a, thereby effectively sterilizing the mouth portion 2a.

In this case, like the light irradiation apparatus 30 shown in FIG. 2(C), it is particularly preferably to arrange the lamp 30a above the mouth portion 2a and arrange the reflector plate 31 to surround the lamp 30a. With such an arrangement, the inner and outer surfaces of the mouth portion 2a can be efficiently irradiated with the light L.

The preform 1 is then conveyed into the heating furnace from the heating furnace conveying wheel 17, and as shown in FIG. 2(D), the preform 1 is heated to a temperature suitable for the subsequent blow molding by the infrared heater 18a or other heating device. As shown in FIG. 2(D), the spindle 29 is inserted into the mouth portion 2a of the preform 1, so that the preform 1 suspended in the upright position (or inverted position) and rotating with the spindle 29 is conveyed into the heating furnace 25 by the endless chain 18. Spindles 29 are attached to the endless chain 18 at regular intervals. The spindle 29 is capable of rotating, and the endless chain 18 is rotated by the pulleys 26a and 26b. The hydrogen peroxide, which is a constituent of the sterilizer, on the preform 1 is decomposed by this heating, and bacteria or the like on the surface of the preform 1 is killed. An excessive hydrogen peroxide or other constituents of the sterilizer is volatilized by the heating.

The infrared heater 18a is preferably a halogen lamp that emits infrared rays. As the infrared heater 18a, a plurality of halogen lamps are arranged side by side perpendicularly to the axial direction of the preform 1. The preform 1 is heated by near infrared rays, infrared rays, or far infrared rays emitted from the halogen lamps. The heating temperature of the plurality of halogen lamps may be controlled so that the temperature of the heated preform 1 varies in the axial direction. A plurality of units of halogen lamps are arranged side by side in the direction of movement of the preform 1. The number of units can be arbitrarily determined. The heating temperature of the halogen lamp units may also be controlled so that the preform 1 is heated to a higher temperature in an early stage of heating and to a lower temperature in a later stage of heating.

Although the preform 1 is heated by the infrared rays or the like emitted from the infrared heater 18a, the infrared rays or the like that travel beyond the preform 1 without being absorbed by the preform 1 make no contribution to heating of the preform 1. Thus, a reflector can be provided behind the preform 1 to reflect the infrared rays or the like traveling beyond the preform 1 and efficiently heat the preform 1. The reflector is made of metal and has a surface coated with gold, silver, aluminum or the like by vapor deposition or plating. Any reflector can be used as far as the reflector can reflect the infrared rays or the like. The reflector may be formed by a flat surface, a curved surface or a combination thereof. The reflector may be provided not only behind the preform 1 but also behind the infrared heater 18a to reflect the infrared rays or the like traveling beyond the infrared heater 18a.

As shown in FIG. 10, when a lower part of the spindle 29 is inserted into the mouth portion 2a of the preform 1, the elastic body 29b is elastically deformed, and thereby the preform 1 is supported on the spindle 29. At the same time, if there is the umbrella-shaped member 29a, the mouth portion 2a of the preform 1 is covered by the umbrella-shaped member 29a.

In this case, a gap is formed between the inner surface of the mouth portion 2a of the preform 1 and the lower part of the spindle 29 and between the outer surface of the mouth portion 2a of the preform 1 and the umbrella-shaped member 29a, so that hot air, which is the air containing hydrogen peroxide that is a constituent of the sterilizer vaporized in the preform 1 heated by heat from the infrared heater 18a, flows from inside the preform 1 to outside of the preform 1 through the gap and at the same time heats the mouth portion 2a of the preform 1, and the hydrogen peroxide sterilizes the outer surface of the mouth portion 2a of the preform 1.

Considerations have to be made to prevent the mouth portion 2a of the preform 1 from being deformed by the heat applied before the preform 1 is molded into the bottle 2, in order to compromise the sealing of the bottle 2 with the cap 3 after the preform 1 is molded into the bottle 2. The hot air flowing in the gap described above heats the mouth portion 1a to a temperature equal to or lower than 70° C. This is because the mouth portion 2a is deformed at a temperature 70° C. higher.

The heated preform 1 may be released from the spindle 29, passed to the gripper 13 on the wheel 19, and conveyed to the mold 4, which is a blow-molding die, shown in FIG. 3(E) while aseptic air is blasted to the preform 1 from the side of the mouth portion 2a thereof. The preform 1 is fed to the mold 4 while the aseptic condition thereof is maintained by the blasting of the aseptic air. By heating the aseptic air, the preform 1 can be fed to the mold 4 while preventing the temperature of the preform 1 from lowering.

Alternatively, the preform 1 may be irradiated with light containing ultraviolet rays on the wheel 19 as shown in FIG. 2(C).

The heated preform 1 is molded in the same manner as in the first embodiment. The molded bottle 2 is grasped by the gripper 13 and conveyed to the inspection apparatus 27 by the wheel 21. Although not shown, the inspection apparatus 27 can be provided with a light source and a camera for inspecting whether the top surface of the mouth portion 2a of the molded bottle 2 is smooth or not, for example. If the inspected bottle 2 is defective, the bottle 2 is removed from the conveying path by a removing apparatus (not shown). Only the bottles 2 that are not determined to be defective are conveyed to the wheel 22. The bottle 2 that is not determined to be defective is conveyed to the filling apparatus by the wheel 22.

As shown in FIG. 12, the wheels 15 and 16 are shielded by the sterilizer blasting chamber 28a. An exhaust device formed by a filter 36 that filters air in the sterilizer blasting chamber 28a and a blower 35 is connected to the sterilizer blasting chamber 28a. Any excessive sterilizer gas blasted from the sterilizer gas blasting nozzle 6 is removed by the filter 36 of the exhaust device and discharged to the outside of the sterilizer blasting chamber 28a. Therefore, the hydrogen peroxide in the sterilizer can be prevented from flowing into the adjacent heating furnace 25 or blow-molding machine 12. The amount of air supplied to or discharged from the sterilizer blasting chamber 28a is desirably adjusted so that the pressure in the sterilizer blasting chamber 28a is a negative pressure lower than the atmospheric pressure.

As shown in FIG. 12, the heating furnace 25 is shielded by the heating section chamber 28b, and the blow-molding machine 12 is shielded by the molding section chamber 28c. Gas or mist of the sterilizer or a mixture thereof is blasted into the heating section chamber 28b and the molding section chamber 28c before operation, and after that, the interior of the heating section chamber 28b and the molding section chamber 28c for aseptic hot air is further sterilized by blasting aseptic hot air. During operation, aseptic air is supplied to the heating section chamber 28b and the molding section chamber 28c to adjust the pressure in the heating section chamber 28b and the molding section chamber 28c to be a positive pressure, thereby maintaining the aseptic condition in the heating section chamber 28b and the molding section chamber 28c. The aseptic air can be obtained by sterilizing air from a blower through a sterilizing filter.

The interior of the heating section chamber 28b is heated by the infrared heater 18a, so that an ascending air current occurs in the heating section chamber 28b. The aseptic air can more smoothly flow without causing a turbulence in the heating section chamber 28b if the aseptic air flows in the same direction as the ascending air current than if the aseptic air flows from above to below. Therefore, the aseptic air is blasted from a lower part to an upper part of the heating section chamber 28b. The aseptic air blasted from the lower part flows upward inside and outside of the infrared heater 18a and the reflector.

The aseptic air flowing from below to above in the heating section chamber 28b contains constituents of the sterilizer volatilized from the preform 1. In order to appropriately keep the pressure in the heating section chamber 28b and discharge the constituents of the sterilizer, an exhaust apparatus is provided on top of the heating section chamber 28b. The exhaust apparatus includes a filter that filters air and a blower. Hydrogen peroxide, which is a constituent of the sterilizer, is decomposed by the filter and discharged.

A filling section chamber that shields the filling section and a sealing section is also sterilized before operation, and the aseptic condition in the chamber is maintained by keeping the interior of the chamber at a positive pressure by aseptic air. The pressure kept at a positive pressure is set at the maximum pressure in the filling section chamber and at lower pressures in more upstream chambers such as the molding section chamber 28c and the heating section chamber 28b. For example, the pressure in the filling section chamber is set at 30 Pa to 150 Pa, the pressure in the molding section chamber 28c is set at 20 Pa to 30 Pa, and the pressure in the heating section chamber 28b is set at 0 Pa to 20 Pa. The pressure in an outlet chamber, which is located downstream of the sealing section and discharges the aseptic product on a conveyor out of the aseptic filling machine, is set at 0 Pa to 20 Pa.

To keep each chamber at a positive pressure, each chamber is provided with an aseptic air supplying apparatus. However, the aseptic air supplying apparatus does not have to be provided on all the chambers. For example, the interior of the molding section chamber 28c may be kept at a positive pressure by the aseptic air flowing from the filling section chamber to the molding section chamber 28c. Furthermore, to keep the pressure in each chamber at an appropriate pressure, each chamber may be provided with an exhaust apparatus. The exhaust apparatus does not have to be provided on all the chambers. For example, the exhaust apparatus provided on the heating section chamber 28b may be used to keep the interior of the molding section chamber 28c at an appropriate pressure.

To ensure the aseptic condition of the molding section chamber 28c, the interior of the molding section chamber 28c is sterilized before operation. However, to prevent inspection equipment from being damaged by the sterilizer, the inspection equipment such as the camera or the lamp may be sealed.

In the following, the second embodiment of the present invention will be described with regard to examples.

(Method of Operation)

A preform 1 having a weight of 20 g that is intended for a 500 ml bottle made of polyethylene terephthalate was used. $10^3$, $10^4$ and $10^5$ B. atrophaeus spores were put on the inner surface of the preform 1 at a total of nine points including three points in the mouth portion, three points in a middle portion of the body, and three points in a bottom portion and air-dried, thereby providing a bacteria-contaminated preform 1.

Then, the light irradiation apparatus 30 provided with the xenon flash lamp 30a and the dome-shaped reflector plate 31 surrounding the lamp 30a as shown in FIG. 2(C) was used to intensively irradiate the inner and outer surfaces of the mouth portion 1a of the preform 1 with light. The lamp was a xenon lamp (having an arc length of 500 nm) available from Econos Japan Co. Ltd., and a pulse of 0.2 sec/time was irradiated six times (the light irradiation step).

Then, the sterilizer gas was blasted to the bacteria-contaminated preform 1 from the sterilizer gas blasting nozzle 6 shown in FIG. 2(A) (the sterilizer gas blasting step). The sterilizer gas was generated by supplying compressed air having a pressure of 0.5 MPa and the sterilizer at a flowrate of 10 ml/min to the sterilizer gas generator 7 shown in FIG. 4. The surface temperature of the evaporating portion 9 was set at 300° C.

Then, as shown in FIG. 2(D), the preform 1 was heated in the heating furnace 25 until the temperature of the outer surface of the body portion of the preform 1 reaches 120° C. (the heating step). Furthermore, as shown in FIG. 3(E), the preform 1 was molded in the mold 4 into a 500 ml bottle 2.

(Method of Measuring Sterilization Effect)

The molded bottle 2 was filled with 100 ml of SCD bouillon medium in an aseptic atmosphere and sealed with a sterilized cap. The sealed bottle 2 was shaken to make the medium come into contact with the whole of the inner surface of the bottle 2, and cultivation was performed at 35° C. for one week. If the medium became opaque, the sterilization was determined to be insufficient. If the medium did not become opaque, the sterilization was determined to be sufficient.

(Method of Measuring Amount of Hydrogen Peroxide Remaining in Bottle)

The molded bottle 2 was filled with 500 ml of pure water and sealed. After that, the concentration of hydrogen peroxide in the pure water was measured by SUPER ORITECTOR MODEL5 available from Chiyoda Manufacturing Co. Ltd.

Examples, Comparative Examples and Results

Table 2 shows examples and comparative examples in which the same operation as that described in Method of Operation was performed. Table 2 shows operational conditions of the examples and comparative examples such as the composition of the sterilizer and the presence or absence of irradiation with light containing ultraviolet rays, the sterilization effect, and the amount of hydrogen peroxide remaining in the bottle.

the hydrogen peroxide remaining in the bottle 2 molded from the preform 1 can be reduced.

In the following, a third embodiment of the present invention will be described with reference to the drawings.

Third Embodiment

The third embodiment of the present invention differs from the first embodiment in that the sterilizer blasted to the preform 1 contains hydrogen peroxide but does not have to contain the solvent, and irradiation of the preform 1 with light containing ultraviolet rays is essential. According to the third embodiment, an aseptic preform can be simply obtained by sterilizing the preform, and the amount of the hydrogen peroxide remaining on the bottle molded from the aseptic preform can be reduced.

(Overview of Method and Apparatus)

As shown in FIG. 1, an aseptic filling system incorporating a sterilizing apparatus for a preform according to this embodiment includes the preform feeding apparatus 11, the preform conveyor 14 that conveys the preform 1 fed from the preform feeding apparatus 11, the heating furnace 25 that heats the preform 1, and the blow-molding machine 12 that molds the preform 1 heated in the heating furnace 25 into a bottle 2.

TABLE 2

| | COMPOSITION OF STERILIZER (% BY MASS) | | | | | REMAINING HYDROGEN |
|---|---|---|---|---|---|---|
| | HYDROGEN PEROXIDE | ETHANOL | WATER | LIGHT IRRADIATION | STERILIZATION EFFEC | PEROXIDE (ppm) |
| EXAMPLE 10 | 30 | 14 | 56 | PRESENCE | ○ | 0.04 |
| EXAMPLE 11 | 20 | 43 | 37 | PRESENCE | ○ | 0.02 |
| EXAMPLE 12 | 15 | 57 | 28 | PRESENCE | ○ | 0.01 |
| EXAMPLE 13 | 10 | 71 | 19 | PRESENCE | ○ | 0.03 |
| EXAMPLE 14 | 5 | 85 | 9 | PRESENCE | ○ | 0.02 |
| EXAMPLE 15 | 1 | 93 | 2 | PRESENCE | ○ | 0.01 |
| COMPARATIVE EXAMPLE 5 | 35 | 0 | 65 | PRESENCE | ○ | 0.08 |
| COMPARATIVE EXAMPLE 6 | 20 | 0 | 80 | ABSENCE | x | 0.04 |
| COMPARATIVE EXAMPLE 7 | 15 | 0 | 85 | PRESENCE | x | 0.04 |
| COMPARATIVE EXAMPLE 8 | 0 | 100 | 0 | PRESENCE | x | <0.01 |

In the table, a circle represents that the sterilization was determined to be perfect in the measurement of sterilization effect.

According to the examples described above, when a sterilizer containing 30% by mass or less of hydrogen peroxide and ethanol having a boiling point of 85° C. or lower as a solvent is used, the preform 1 can be sufficiently sterilized, and the amount of the hydrogen peroxide remaining in the bottle 2 molded from the preform 1 can be reduced. If the content of hydrogen peroxide is greater than 30% by mass, the sterilization can be sufficiently achieved, but the amount of the remaining hydrogen peroxide is high even if the sterilizer does not contain ethanol. If the content of hydrogen peroxide is equal to or less than 30% by mass, the sterilization is insufficient if the sterilizer contains no ethanol. Even if the content of hydrogen peroxide is equal to or less than 5% by mass, if the sterilizer contains ethanol, the preform 1 can be sufficiently sterilized, and the amount of (Overview of Process Performed by Aseptic Filling System)

The preform 1 grasped by the gripper 13 is passed to the wheel 15 following the preform conveyor 14 and irradiated with the light L containing ultraviolet rays while traveling on the wheel 15 as shown in FIG. 2(C) (the light irradiation step).

The sterilizer gas G is blasted to the preform 1 on the wheel 15 from the sterilizer gas blasting nozzle 6 as shown in FIG. 2(A) (the sterilizer gas blasting step).

After that, the preform 1 is passed to the wheel 16, and the air P is blasted to the preform 1 from the air nozzle 37 as shown in FIG. 2(B).

Although the irradiation with the light L (the light irradiation step) and the blasting of the sterilizer gas G to the preform 1 (the sterilizer gas blasting step) are essential, the blasting of the air P (the air blasting step) may not be performed. However, all these steps are desirably performed. Although the blasting of the sterilizer gas G to the preform 1 (the sterilizer gas blasting step) and the blasting of the air P (the air blasting step) are performed in this order, the light irradiation step can be performed at any time.

That is, along the wheel 15, the light irradiation apparatus 30 may be disposed upstream or downstream of the nozzle 6. Furthermore, the light irradiation apparatus 30 may be disposed downstream of the location where the blasting of air (the air blasting step) is performed along the wheel 16. Furthermore, the irradiation with the light L (the light irradiation step), the blasting of the sterilizer gas G (the sterilizer gas blasting step), and the blasting of air P (the air blasting step) may be performed on a single wheel or different wheels.

The sterilized preform 1 is released at the heating furnace conveying wheel 17 from the gripper 13 that has grasped the preform 1 being conveyed by the sterilizer gas blasting wheel 15, and conveyed to the heating furnace 25 by the heating furnace conveying wheel 17.

The heating step for the preform 1, the blow molding of the heated preform into the bottle 2, the inspection of the molded bottle 2, the filling of the inspected bottle with the content, and the sealing of the filled bottle 2 are the same as those in the first embodiment.

(Details of Method and Apparatus for Sterilizing Preform)

The preform 1 on the wheel 15 is irradiated with the light containing ultraviolet rays as shown in FIG. 2(C) (the light irradiation step). This step may be performed plural times. Specifically, this step may be performed before the blasting of the sterilizer gas G to the preform 1 (the sterilizer gas blasting step) and after the blasting of the air P (the air blasting step). The light irradiation apparatus 30 that irradiates the preform 1 with light and the light in the third embodiment are the same as those in the first embodiment.

If the mouth portion 2a is deformed by heating, the aseptic condition of the product filled with a drink shown in FIG. 3(H) is compromised. Conventionally, deformation of the mouth portion 2a is prevented by reducing the amount of hot air P blasted to the outer surface when the air P is hot air, or by reducing the temperature in the heating furnace 25 during heating for blow molding. This may lead to insufficient sterilization of the mouth portion 2a. To avoid this, conventionally, an excessive amount of sterilizer is blasted to the mouth portion 2a for sterilization. According to the present invention, the light irradiation apparatus 30 is provided with the reflector plate 31, and the mouth portion 2a is intensively irradiated with the light L, so that the mouth portion 2a can be effectively sterilized, and poor sterilization of the mouth portion 2a can be avoided even if the amount of the sterilized blasted is reduced.

In this case, like the light irradiation apparatus 30 shown in FIG. 2(C), it is particularly preferable to arrange the lamp 30a above the mouth portion 2a and arrange the reflector plate 31 to surround the lamp 30a. With such an arrangement, the inner and outer surfaces of the mouth portion 2a can be efficiently irradiated with the light L.

The sterilizer according to the third embodiment contains at least hydrogen peroxide. An appropriate content of hydrogen peroxide falls within a range from 0.5% by mass to 65% by mass. If the content is less than 0.5% by mass, the sterilizing power may be insufficient. If the content is more than 65% by mass, it is difficult to safely handle the sterilizer. Furthermore, a more preferable content is 0.5% by mass to 40% by mass. If the content is equal to or less than 40% by mass, the sterilizer can be more easily handled, and the amount of the remaining hydrogen peroxide after sterilization can be reduced because of the low concentration.

Although the sterilizer contains water, the sterilizer may contain one or more of alcohols such as methyl alcohol, ethyl alcohol, isopropyl alcohol, n-propyl alcohol and butyl alcohol, ketones such as acetone, methyl ethyl ketone and acetyl acetone, and glycol ethers, for example.

The sterilizer may further contain an additive agent such as a compound having a sterilizing effect such as peracetic acid, acetic acid, a chlorine compound or ozone, a cationic surface active agent, a non-ionic surface active agent, and a phosphate compound.

As in the first embodiment, the sterilizer is gasified by the sterilizer gas generator 7 shown in FIG. 4. Although the amount of the blasted sterilizer gas G is arbitrary, the amount of the blasted sterilizer gas G depends on the amount of the sterilizer supplied to the sterilizer gas generator and the duration of the blasting. A plurality of sterilizer gas generators may be provided. Although the amount of the blasted sterilizer gas G varies with the size of the preform, an appropriate amount of hydrogen peroxide falls within a range from $1\times10^{-3}$ g/mm$^2$ to 1 g/mm$^2$. If the amount of hydrogen peroxide is less than $1\times10^{-3}$ g/mm$^2$, the sterilization is sufficient. If the amount of hydrogen peroxide is more than 1 g/mm$^2$, the amount of the hydrogen peroxide remaining on the preform 1 is high.

The sterilizer gas G is blasted to the preform 1 from the sterilizer gas blasting nozzle 6. The blasting of the sterilizer gas is the same as that in the first embodiment.

Immediately before the blasting of the sterilizer gas G to the preform 1 shown in FIG. 2(A), the preform 1 may be preliminarily heated by blasting heated air to the preform 1. The preliminary heating can further improve the sterilization effect on the preform 1.

The preform 1 to which the sterilizer gas has been blasted may be grasped by the gripper 13 as shown in FIG. 2(B), and the air P may be blasted to the preform 1 from the air nozzle 37 while the preform 1 is being conveyed.

The blasted air P activates the hydrogen peroxide on the surface of the preform 1, and the activated hydrogen peroxide kills the bacteria on the inner and outer surfaces of the preform 1. In addition, by blasting the air P, the sterilizer on the preform 1 is quickly removed from the surface of the preform 1. Since the sterilizer on the preform 1 is removed from the preform 1 by the blasting of the air P before the preform 1 enters the heating furnace 25, various devices such as a seal member in the blow-molding machine 12 are prevented from being damaged by hydrogen peroxide. In addition, whitening, distortion, uneven molding or other defects of the bottle due to the sterilizer on the preform 1 can be prevented.

The air P can be at room temperature. However, hot air, which is the air P heated, promotes decomposition of hydrogen peroxide to improve the sterilization effect and reduces the amount of the remaining hydrogen peroxide. The air is desirably heated in such a manner that the temperature of the air is 40° C. to 140° C. when the air is blasted to the preform. If the temperature is lower than 40° C., the effect of the heating is not significant, and if the temperature of the preform 1 is higher than 70° C., deformation or other defects of the mouth portion 2a of the preform 1 occurs. For this reason, the temperature of the hot air preferably does not exceed 140° C.

As shown in FIG. 2(B), the air P is blasted through the slit-shaped air blasting port 37a formed in the box-shaped manifold 37b that is the main body of the air nozzle 37.

Furthermore, as shown in FIG. 6(A), the box-shaped manifold 37b of the air nozzle 37 is curved along the arc of the wheel 16, and the slit-shaped air blasting port 37a is formed in the bottom surface of the manifold 37b. The air nozzle 37 is arranged on the wheel 16 in such a manner that the air blasting port 37a extends along the traveling path of the preform 1 on the wheel 16. In addition, as shown in FIG. 6(B), the blower 32, a HEPA filter 33 and the electric heater 34 are connected to the manifold 37b. Outside air taken in by the blower 32 is sterilized by the HEPA filter 33 and heated by the electric heater 34, and the resulting hot air P is fed into the air nozzle 37.

The air supplied to the air nozzle 37 may not be the air from the blower 32 but may be compressed air having higher driving force sterilized by a sterilizing filter. Alternatively, high-pressure air used for blow molding in the blow-molding machine 12 may be collected and reused.

As shown in FIG. 6(B), the air P supplied into the manifold 37b of the air nozzle 37 jets from the air blasting port 37a and is blasted to the preform 1 traveling below the air blasting port 37a with the mouth portion 2a facing up, and some of the air P flows into the preform 1, and other of the air P flows along the outer surface of the preform 1.

As in the first embodiment, sterilized air P may be blasted to the preform 1 from the tubular air blasting nozzle 38 shown in FIGS. 7 and 8 or the air nozzle 40 shown in FIG. 9.

The preform 1 is then conveyed into the heating furnace 25 by the heating furnace conveying wheel 17, and as shown in FIG. 2(D), the preform 1 is heated to a temperature suitable for the subsequent blow molding by the infrared heater 18a or other heating device. The heating is performed in the same manner as in the first embodiment. The hydrogen peroxide remaining on the preform 1 may be further decomposed by this heating, and sterilization of the preform 1 may be further promoted. As a result, the amount of the remaining hydrogen peroxide may be further reduced.

The heated preform 1 is released from the spindle 29 and passed to the gripper 13, and may be conveyed to the mold 4, which is a blow-molding die, shown in FIG. 3(E) while aseptic air Q is blasted to the preform 1 from the side of the mouth portion 2a thereof as shown in FIG. 11. The preform 1 is fed to the mold 4 while the aseptic condition thereof is maintained by the blasting of the aseptic air Q.

The aseptic air Q described above may be hot air. By blasting hot air, the temperature of the preform 1 is prevented from lowering.

As in the first embodiment, the heated preform 1 is blow-molded into the bottle 2 in the mold 4 as shown in FIG. 3(E). The molded bottle 2 is grasped by the gripper 13 and conveyed to the inspection apparatus 27 by the wheel 21. Although not shown, the inspection apparatus 27 can be provided with a light source and a camera for inspecting whether the top surface of the mouth portion 2a of the molded bottle 2 is smooth or not, for example. If the inspected bottle 2 is defective, the bottle 2 is removed from the conveying path by a removing apparatus (not shown). Only the bottles 2 that are not determined to be defective are conveyed to the wheel 22. The bottle 2 that is not determined to be defective is conveyed to the filling apparatus by the wheel 22.

As shown in FIG. 1, the wheels 15 and 16 are surrounded by the chamber 28a. An exhaust device formed by a filter 36 that filters air in the chamber 28a and a blower 35 is connected to the chamber 28a. Any excessive sterilizer blasted from the sterilizer gas blasting nozzle 6 is removed by the filter 36 of the exhaust device and discharged to the outside of the chamber 28a. Therefore, the hydrogen peroxide in the sterilizer can be prevented from flowing into the adjacent heating furnace 25 or blow-molding machine 12. The amount of air supplied to or discharged from the chamber 28a is desirably adjusted so that the pressure in the chamber 28a is a negative pressure lower than the atmospheric pressure.

As shown in FIG. 1, the heating furnace 25 and the blow-molding machine 12 are surrounded by the chamber 28b. The pressure in the chamber 28b is desirably adjusted to be a positive pressure by supplying sterilized air obtained by passing air from a blower through a HEPA filter.

As shown in FIG. 1, the wheel 22 is surrounded by a chamber 28c. Aseptic air is desirably also supplied to the chamber 28c, and the pressure in the chamber 28c is desirably adjusted to be between the pressure of the aseptic air supplied to the filling apparatus where the bottle 2 is filled with the content in the subsequent step and the pressure in the chamber 28b.

By maintaining the interior of the chambers 28b and 28c at a positive pressure by supplying aseptic air, bacteria can be prevented from entering the chambers from outside, and the aseptic condition in the chambers that is achieved by sterilization before operation can be maintained. The sterilization before operation may be gas sterilization of the interior of the chambers 28a, 28b and 28c by a hydrogen peroxide gas having a concentration of 10 mg/L or less, for example. Alternatively, portions of the chambers that are to come into contact with the preform 1 or the bottle 2 may be irradiated with light containing ultraviolet rays. Alternatively, a chemical containing 1% by mass of ethanol or hydrogen peroxide may be sprayed to portions that are to come into contact with the devices, such as the mold 4, the blow nozzle 5 and the gripper 13.

The present invention is configured as described above. However, the present invention is not limited to the embodiments described above, and various modifications can be made without departing from the spirit of the present invention.

REFERENCE SIGNS LIST 1 preform
2 bottle
6 sterilizer gas blasting nozzle
6a, 6b nozzle
9 evaporating portion
23 umbrella-shaped member
24 gas blasting port
37 air nozzle
37a air blasting port
G gas
P air
L light

The invention claimed is:
1. A method for sterilizing a preform, comprising:
a light irradiation step of irradiating at least a mouth portion of the preform with light containing ultraviolet rays from a light irradiation apparatus, which is positioned above an opening in the mouth portion of the preform, with the light irradiation apparatus comprising a lamp for emitting the light containing ultraviolet rays and a dome-shaped reflector plate that comprises a plurality of surfaces that surround the lamp and an opening through which the light containing ultraviolet rays is emitted, such that both inner and outer surfaces of the opening in the mouth portion of the preform are irradiated with the light containing ultraviolet rays; and a sterilizer gas blasting step of gasifying a sterilizer containing at least hydrogen peroxide and blasting the sterilizer gas to the preform, wherein the light irradiation step is performed before the sterilizer gas blasting step.

2. The method for sterilizing a preform according to claim 1, wherein the sterilizer gas is generated by spraying the sterilizer into an evaporating portion, and is blasted to the preform from a nozzle of the evaporating portion.

3. The method for sterilizing a preform according to claim 2, wherein the nozzle or a plurality of the nozzles is opposed to a traveling path of the preform, and the sterilizer gas is blasted to the preform from the nozzle or the nozzles.

4. The method for sterilizing a preform according to claim 2, wherein the sterilizer gas is divided into a plurality of flows in the nozzle, one of the flows is directed to the mouth portion of the preform, and another of the flows is directed to an outer surface of the preform.

5. The method for sterilizing a preform according to claim 1, wherein after the sterilizer gas is blasted to the preform, air is blasted to a part of the preform to which the sterilizer gas has been blasted.

6. The method for sterilizing a preform according to claim 5, wherein the air is hot air.

7. The method for sterilizing a preform according to claim 1, wherein the lamp is a xenon flash lamp.

8. The method for sterilizing a preform according to claim 1, wherein the inner and the outer surfaces of the opening in the mouth portion of the preform are intensively irradiated with the light containing ultraviolet rays.

9. The method for sterilizing a preform according to claim 1, wherein the sterilizer at least contains 30% by mass or less of hydrogen peroxide and a solvent having a boiling point of 85° C. or lower.

10. The method for sterilizing a preform according to claim 1, wherein the sterilizer is a solution containing 0.5% by mass to 30% by mass of a hydrogen peroxide constituent and 14% by mass to 99% by mass of ethanol.

11. An apparatus for sterilizing a preform, comprising:

a transfer device that transfers the preform from a stage of supplying the preform to a stage of molding the preform into a bottle;

a nozzle that blasts a sterilizer gas to the preform on the transfer device; and a light irradiation apparatus that irradiates at least a mouth portion of the preform with light containing ultraviolet rays, the light irradiation apparatus is positioned above an opening in the mouth portion of the preform, with the light irradiation apparatus comprising a lamp for emitting the light containing ultraviolet rays and a dome-shaped reflector plate that comprises a plurality of surfaces that surround the lamp and an opening through which the light containing ultraviolet rays is emitted, such that both inner and outer surfaces of the opening in the mouth portion of the preform are irradiated with the light containing ultraviolet rays, wherein the light irradiation apparatus is disposed upstream of the nozzle.

12. The apparatus for sterilizing a preform according to claim 11, wherein the nozzle is a nozzle that blasts, to the preform, the sterilizer gas at least containing 30% by mass or less of hydrogen peroxide and a solvent having a boiling point of 85° C. or lower.

13. The apparatus for sterilizing a preform according to claim 11, wherein the sterilizer is a solution containing 0.5% by mass to 30% by mass of a hydrogen peroxide constituent and 14% by mass to 99% by mass of ethanol.

14. The apparatus for sterilizing a preform according to claim 11, wherein an air nozzle that blasts air to the preform is arranged downstream of the nozzle along the transfer device.

15. The apparatus for sterilizing a preform according to claim 14, wherein the air nozzle has a slit-shaped blasting port that blasts the air to the opening in the mouth portion of the preform, and the blasting port extends along a direction of transfer of the preform.

16. The apparatus for sterilizing a preform according to claim 11, wherein the nozzle is disposed at a tip end part of an evaporating portion that gasifies the sterilizer by spraying the sterilizer.

17. The apparatus for sterilizing a preform according to claim 11, wherein the nozzle that feeds the sterilizer gas is divided into a plurality of pipelines, a discharge port of one of the pipelines is opposed to the opening in the mouth portion of the preform, another of the pipelines extends along an outer surface of the preform, and a discharge port of the another pipeline is opposed to the outer surface of the preform.

18. The apparatus for sterilizing a preform according to claim 11, wherein the lamp is a xenon flash lamp.

19. The apparatus for sterilizing a preform according to claim 11, further comprising:

the reflector plate arranged on a side of the lamp that is opposite to the opening in the mouth portion of the preform.

20. The apparatus for sterilizing a preform according to claim 19, wherein the reflector plate is arranged to cover the opening in the mouth portion of the preform.

* * * * *